(12) United States Patent
Sahadevan

(10) Patent No.: US 9,555,264 B1
(45) Date of Patent: Jan. 31, 2017

(54) MEMS BASED PARALLEL MICROBEAM RADIOSURGERY WITHOUT ADAPTIVE RESISTANCE TO RADIATION

(71) Applicant: Velayudhan Sahadevan, Beckley, WV (US)

(72) Inventor: Velayudhan Sahadevan, Beckley, WV (US)

( * ) Notice: Subject to any disclaimer, the term of this patent is extended or adjusted under 35 U.S.C. 154(b) by 162 days.

(21) Appl. No.: 14/325,355

(22) Filed: Jul. 7, 2014

Related U.S. Application Data

(63) Continuation-in-part of application No. 12/929,770, filed on Feb. 15, 2011, now Pat. No. 8,915,833.

(51) Int. Cl.
*A61N 5/01* (2006.01)
*A61N 5/10* (2006.01)

(52) U.S. Cl.
CPC .......... *A61N 5/1007* (2013.01); *A61N 5/1084* (2013.01); *A61N 2005/1019* (2013.01)

(58) Field of Classification Search
None
See application file for complete search history.

(56) References Cited

U.S. PATENT DOCUMENTS

| 4,147,562 A | 4/1979 | Chiang |
| 5,339,347 A | 8/1994 | Slatkin |
| 8,173,983 B1 | 5/2012 | Sahadevan |
| 2001/0038680 A1 | 11/2001 | Davidson |
| 2003/0215052 A1 | 11/2003 | Grodzins |
| 2007/0280408 A1* | 12/2007 | Zhang ............... A61B 6/025 378/10 |
| 2010/0038597 A1* | 2/2010 | Reynolds ............. C09D 5/24 252/500 |
| 2010/0329413 A1* | 12/2010 | Zhou .................. A61N 5/10 378/4 |

OTHER PUBLICATIONS

Cao N. et al, NF-kB Mediated HER2 Overexpression in Radiation-Adaptive Resistance, Radiat Res. Jan. 2009; 171(1): 9-21, Abstract lines 7-8 and p. 7, paragraph 3.

(Continued)

*Primary Examiner* — Charlie Y Peng

(57) ABSTRACT

This invention relates to MEMS X-ray sources based on carbon nanotube coated with metal oxides and metal oxide crystals and insulated with parylene for parallel microbeam intraoperative 100 to 1,000 Gy radiation therapies with minimal toxicity to normal tissue. It sterilizes cancer stem cells that cause tumor recurrence and metastasis. It generates high brightness, 10,000 to 20,000 Gy/s radiations that is closer to synchrotron radiation's dose rate.

The parallel microbeam generating X-ray sources are microfabricated with CNT and its variant herringbone, stacked carbon nanotube. They are implantable or contact therapy X-ray sources. Each microfocus carbon nanotube based X-ray source is capable of switching a series of parallel microbeam simultaneously or in sequence. The 100-1,000 Gy single fraction radiosurgery exposes tumor antigens that induce local and systemic tumor immunity. It avoids adaptive resistance to radiation therapy as with 2 Gy daily fractionated radiation therapies that lasts several weeks.

11 Claims, 32 Drawing Sheets

(56) References Cited

OTHER PUBLICATIONS

Minsky B. et al., Cancer of the Stomach, p. 826, in Text book of Radiation Oncology; Leibel & Phillips ed. 2nd Edition, 2004, Saunders, Philadelphia.
Xu Quing-Yong et al, Identification of differential gene expression profiles of radioresistant lung cancer cell line established by fractionated ionizing radi in vitro.
Lammering, G et al EGFRvIII-mediated radioresistance through a strong cytoprotective response, , Oncogenic (2003) 22, 5545-5553, Abstract, col. 1, lines 1-18.
Bipasha Mukherjee et al, EGFRvIII and DNA Double-Strand Break Repair: A Molecular Mechanism for Radiore in Glioblastoma , Cancer Res 2009; 69: (10). May 15, 2009, p. 4252-42.
Hui-Fang Li,et al., Radiation-induced Akt activation modulates radioresistance in human glioblastoma cells, Radiation Oncology 2009, 4:43, p. 1 Abstract-conclu, lines 1-4.
Hui-Fang Li,et al. Radiation-induced Akt activation modulates radioresistance in human glioblastoma cells, Radiation Oncology 2009, 4:43, p. 1 Abstract-conclusion, lines 1-4.
Chakravarty P.K. et al., Dendritic Cells Pulsed with Irradi Prost Tumor Cells—Journal of Cancer Molecu 3(2): 55-60, 2007, p. 59, col. 1, paragraph 5, lines 1-11.
Chakravarty P.K. et al.Dendritic Cells Pulsed with Irradiated Prostate Tumor Cells—Journal of Cancer Molecules 3(2): 55-60, 2007, p. 56, Abstract.
Bei Liu. et al. Minireview, Overcoming Immune Tolerance to Cancer by Heat—1, I., 2002, Molecular Cancer Therapeutics , vol. 1, 1147-1151, Oct. 2002, Abstract p. 1147.
Nation JA et al, Advances in Cold Cathode Physics and Technology, Proceedings of the IEEE, vol. 87, No. 5, May 1999, p. 865, col. 2, parag. 2.
Hu et aCarbon Nanotubes and Carbon Nanotubes/Metal Oxide Heterostructures: Synthesis-Growth and Applications, Naraghi M (Ed.), ISBN: 978-953-307-566-2, InTech: I,p. 18.
Chalamala B. R.et al, Fed Up With Flat Tubes, IEE Spectrum, Apr. 1998, p. 44.
Dale Kubo H et al, High dose-rate brachytherapy treatment delivery: Report of the AAPM Radiation Therapy Committee Task Group No. 59, p. 376, col. 2, paragraph 2.
Pajon F et al, Radiation Resistance of Cancer Stem Cells: The 4 R's of Radiobiology Revisited, Stem Cells 2010;28: p. 639 abstract.
Swant S.G. etal, Adaptive Response and the Bystander Effect Induced by Radiation in C3H 10T½ Cells in Culture, Radiat. Res. 156, 177-180 (2001), abstract lines 7-8.
Kuwhar, Y et al, Enhancement of autophagy is a potential modality for tumors refractory to radiotherapy, Cell Death and Disease (2011) 2, e177; doi:10.1038/cddis.2011.56; p.
Fam M. et al.Nuclear Factor-KB and Manganese Superoxide Dismutase Mediate Adaptive Radiores in Low-Dose Irradiated Mouse Skin Epith Cells, Ming Fan et al, Cancer Res 2007; 67.
Borjesson J. et al, Medical applications of X-ray fluore for trace elem research: JCPDS-Intern Centre for Diffraction Data 2007 ISSN 1097-0002, Abstract.
Meng L. J. et al, X-ray Fluores—Tomogra (XFET)—A Monte Carlo Study, IEEE Trans Nucl Sci. Dec. 2011; 58(6): 3359 3369, Abstract.
Bravin A et al, X-ray phase contrast imaging—from pre-clinical applications towards clinics, Phys. Med. Biol. 58 (2013) R1-R35; Abstract.
Medical Image Sensors and Endoscopy Portugal Awaiba Lda, Madeira Tecnopolo 9020-105 Funchal, Madeira.
Liu,L ,MEMS—Endoscopy, Uni. of Florida, Doctor of Philosophy Thesis, "Large Scan-Range—MEMS Micromirrors and Microlenses and- Biomedical Imaging-" 2013 p. 20.
Newton, R.C., Imaging parenchymal lung diseases with confocal endomicroscopy, Respiratory Medicine (2012) 106, 127e137, Abstract.
Martirosyan N.L. et al, Use of in vivo near-infrared laser—endomicro with indocyanine green to detect the boundary of infilt tumor. J Neurosurg 115:1131—Abstract.
Hutchison D.N et al, Carbon nanotubes as a framework for high aspect ratio MEMS fabrication JMEMS.2009.2035639, Abstract and p. 8.
Wei-Chuan Fang, High Methanol Oxidation Activity of Well-Dispersed Pt Nanoparticles on Carbon Nanotubes Using Nitrogen Doping, Nanoscale Res Lett (2010) 5:68-73, Abstract.
Singh-Jasuja H. et al The heat shock protein gp96: a receptor-targeted cross priming carrier and activator of . . . ., Cell Stress & Chaperones (2000) 5 (5), 462—Abstract.
Yang Lin, T. et al. Proteomics of the Radioresistant phenotype in head and Neck Cancer: Gp96 . . . , 2010, Int. J. Radiation Oncology Biol. Phys., vol. 78, No. 1, pp. 246-25.
Serduc, R. I. et al,High-Precision Radiosurgical Dose Delivery—Microbeam Synchrotron—, PLoS One, vol. 5 | Issue 2, e9028,, p. 11, col. 2, paragraph 2, lines 1-28.
Kalofonos, et al. Enhancement of Monoclonal Antibody Uptake in Human Colon Tumor—Irradiation, , Cancer Res 1990;50:159-163, Abstract, p. 159.
Denardo, S.J. et al, Enhancement of Clinical Radioimmunotherapy—Journal of the National Cancer Institute, vol. 84, No. 6, 1992, 374-375, p. 375, paragraph 2, lines 10-11.
Schaue, D. et al., Links between Innate Immunity and Normal Tissue Radiobiology, Radiat Res. Apr. 2010; 173(4): 406-417, p. 408, paragraph 3, lines 1-18.
Chakraborty, M. et al Irradiation—Tumor Cells—Fas—Enhances CTL Lytic Activity, CTL Adoptive Immunoth, , J Immunol 2003;170; p. 6341, par. 3, lines 21-23, col. 2, line 1-3.
Chakraborty, M. et al Irradiation of Tumor Cells—Fas and Enhances CTL Lytic Activity and CTL Adoptive Immunotherapy, J Immunol 2003;170;6338-6347, p. 6339, Abstra Ii 7-14.
Frelinger, M. J., et al, Radiation-Induced IFN-g Production—Antitumor Immunity, J Immunol 2008;180;3132-3139, p. 3138, col. 2, paragraph 3, lines 1-22.
Frelinger, M. J., et al, Radiation-Induced IFN-g Production—Antitumor Immunity, J Immunol 2008;180;3132-3139, p. 3138, col. 2, paragraph 3, lines 1-17.
Stickney D R et al, Enhancement of monoclonal antibody binding to melanoma with single dose radiation or hyperthermia, [1987(3):47-52 p. 49, Abstract.
Alessandra di Pietro et al, Heat shock protein peptide complex 96-based vaccines in melanoma,—, Human Vaccines 5:11, 727-737; Nov. 2009; p. 727, abstract.
Testori A et al, Phase III Comparison of Vitespen, an Autologus Tumor—Derived Heat Shock Protein gp96 Peptide Complex Vaccine,—Stage IV Melanoma: J Clin Oncol 26: p. 955.
Sahadevan V., U.S. Appl. No. 12/799,949, Abstarct May 6, 2010F.
T. Tuohimma et al. Phase-contrast x-ray imaging with a liquid-metal-jet-anode microfoc source I Appl. Phys. Lett. 91,074104 (2007), Abstract.
Dewhirst M, Vascular Response to Microbeam Radiation Therapy In Vivo Using a Murine Window Chamber Tumor Model 2012 AAPM Annual Meeting Duke University Medical Center.
Bouchet A, et al, Preferen—Effect of Synchro. Microbeam—Intracereb 9L Gliosarcomavascular—Int. J. Radiation Oncology Biol. Phys., vol. 78, No. 5, p. 1503—Abstract.
Martirosyan N.L. et al, Use of in vivo near-infrared laser confocal endomicro—to detect the boundary of infiltra tumor, Neurosurg 115:1131, 2011, Abstract.
High Methanol Oxidation Activity of Well-Dispersed Pt Nanoparticles on Carbon Nanotubes Using Nitrogen Doping, Wei-Chuan Fang, Nanoscale Res Lett (2010) 5:68-73, p. 17-19.
SCS Parylene Properties, SCS coating brochure, p. 1-3.

\* cited by examiner

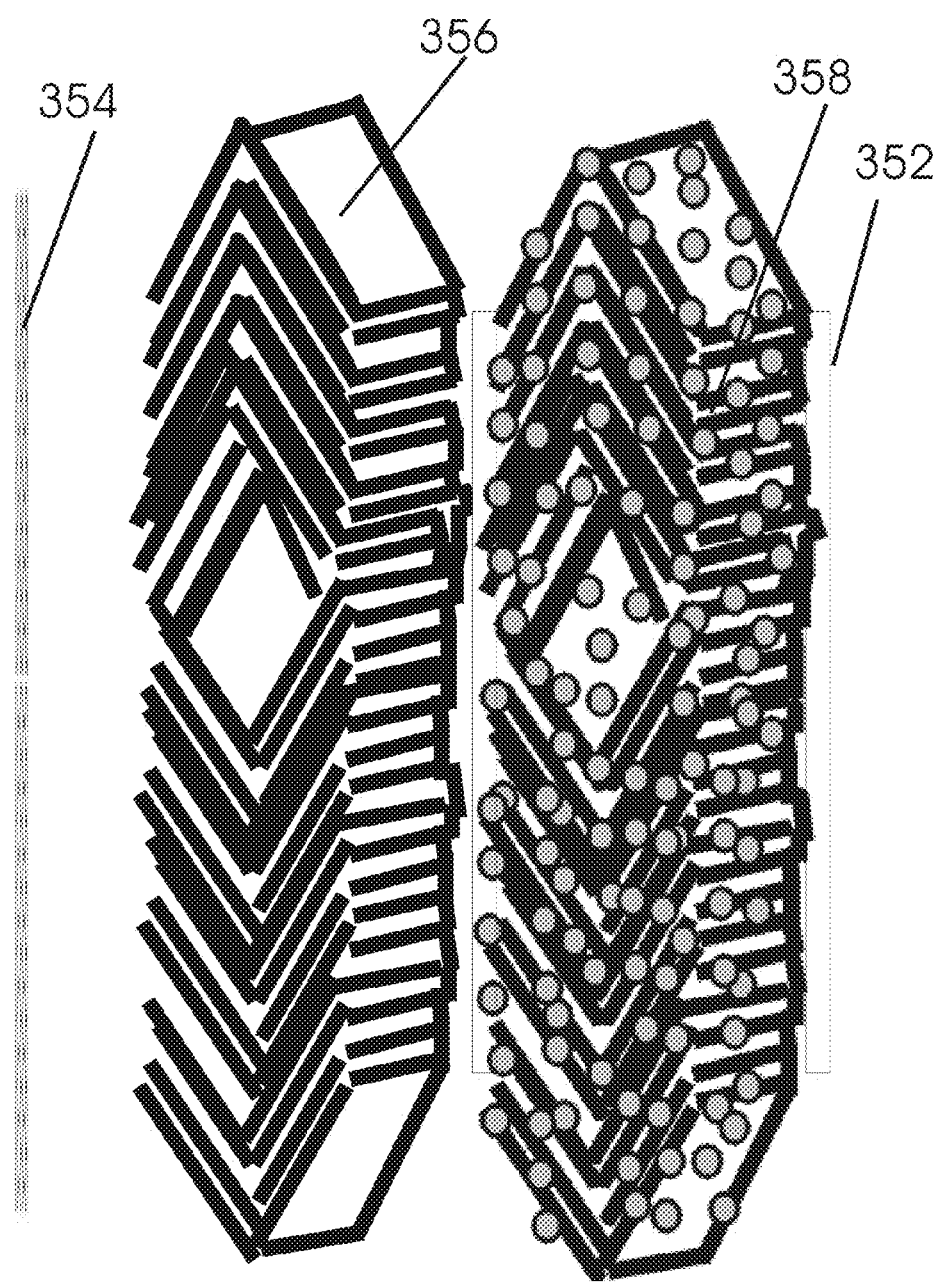

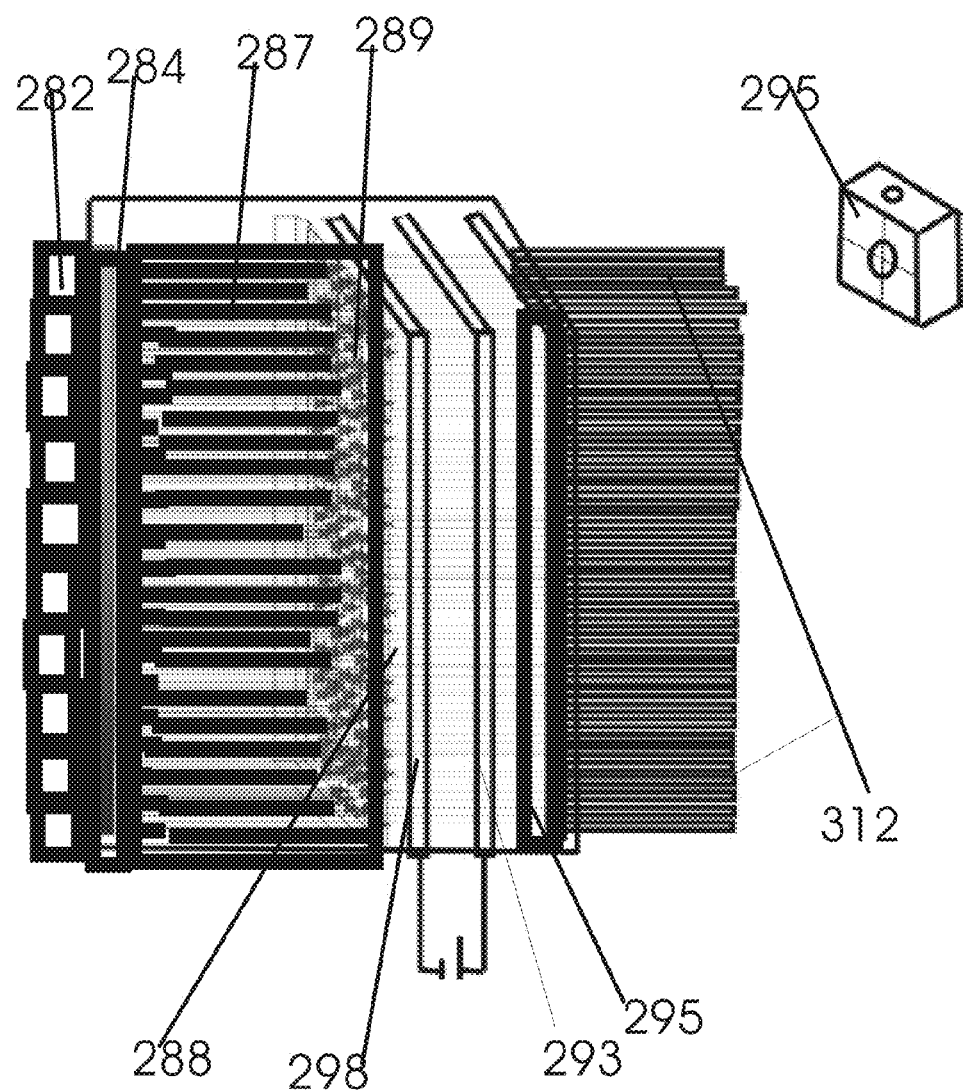

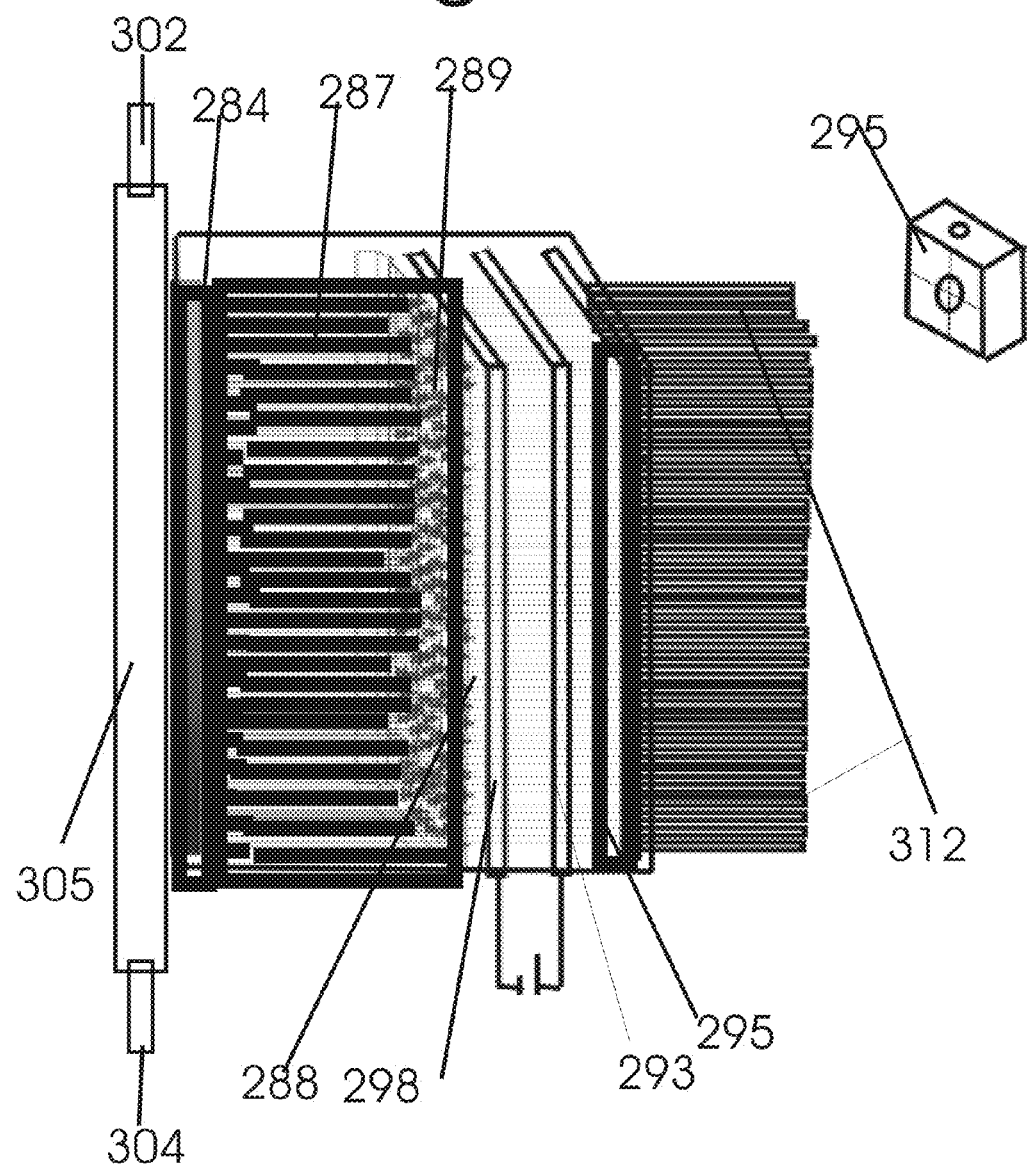

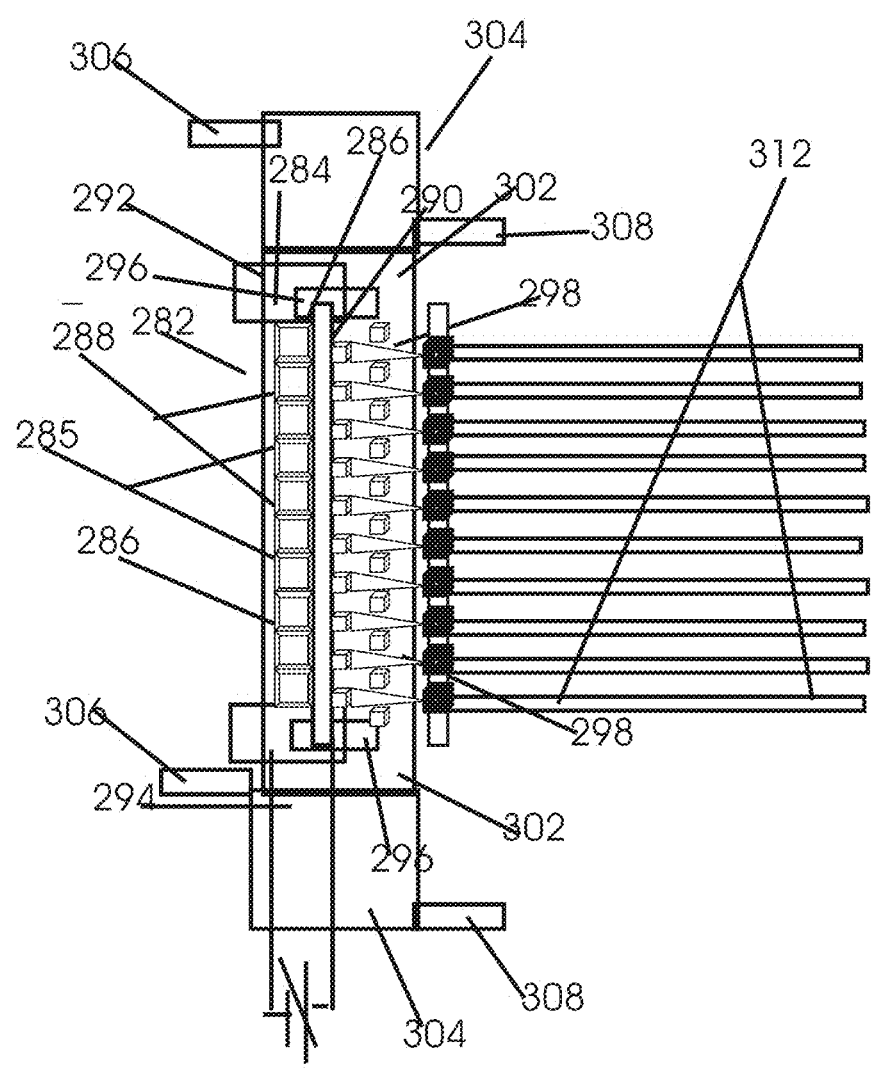

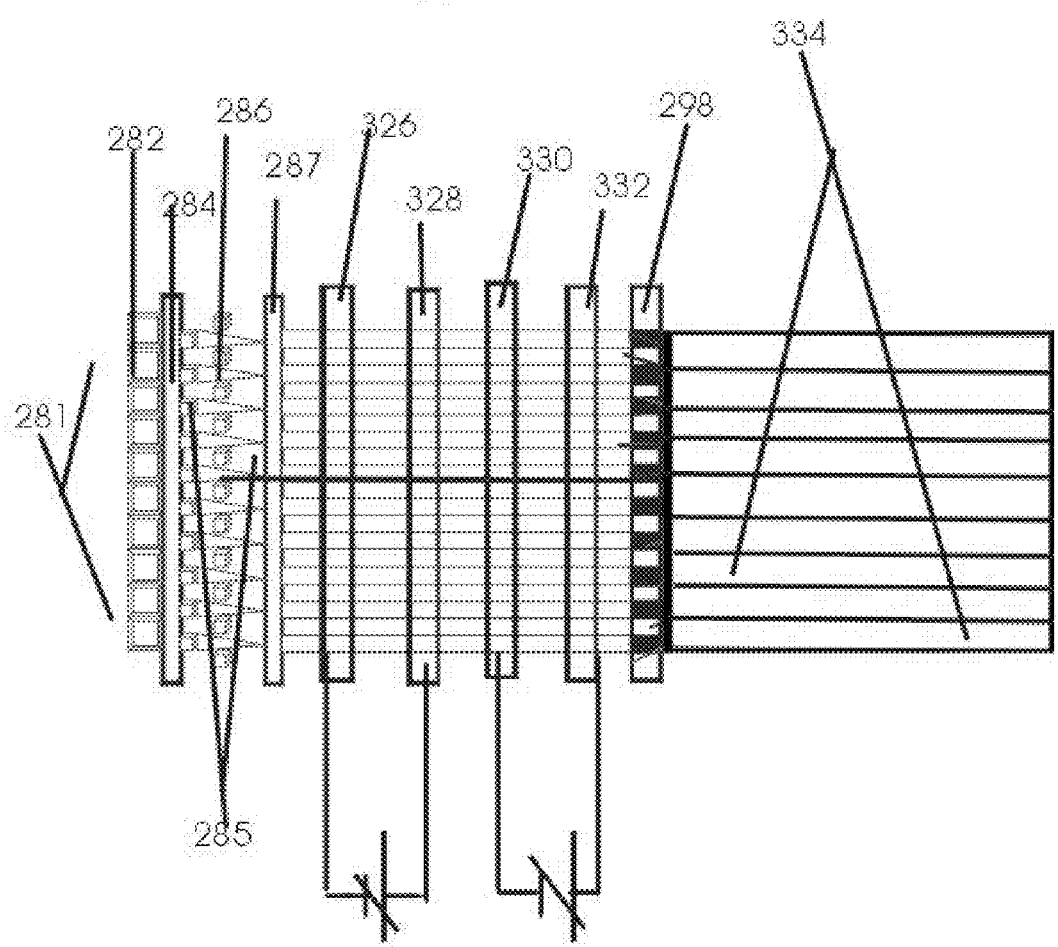

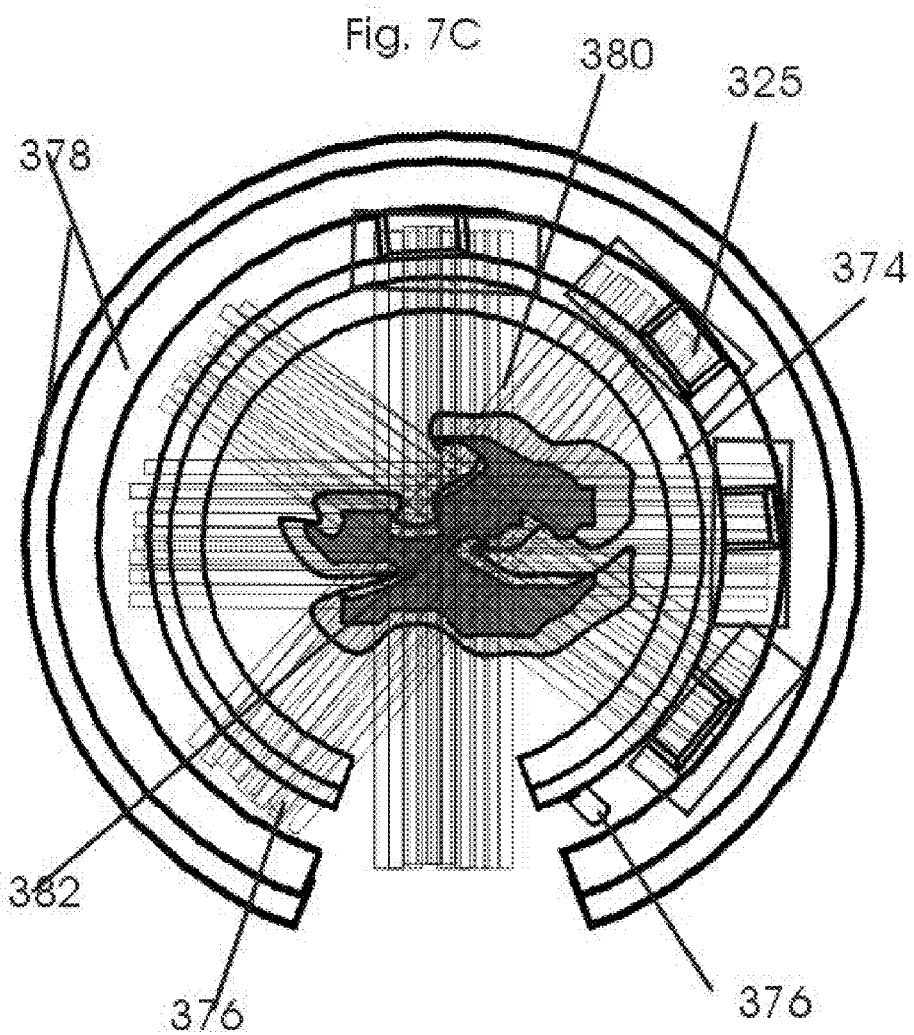

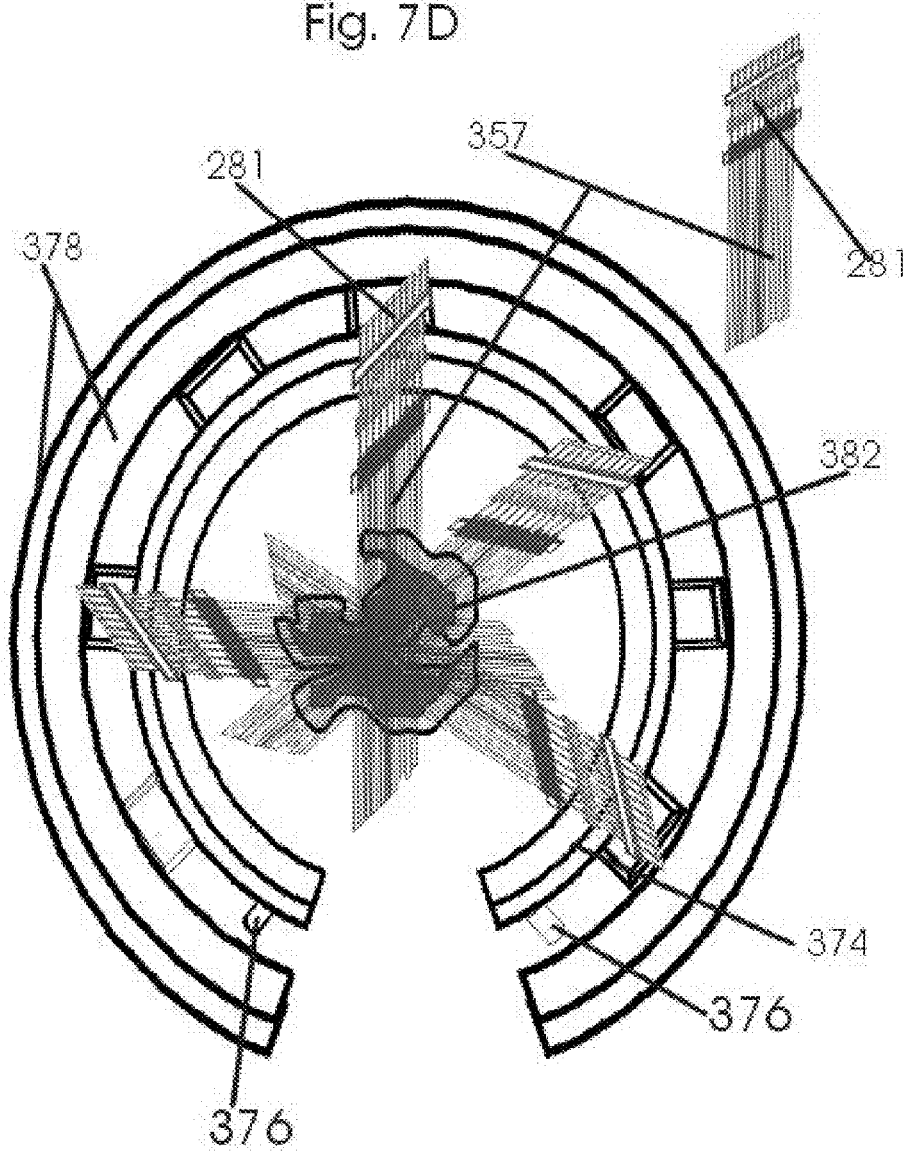

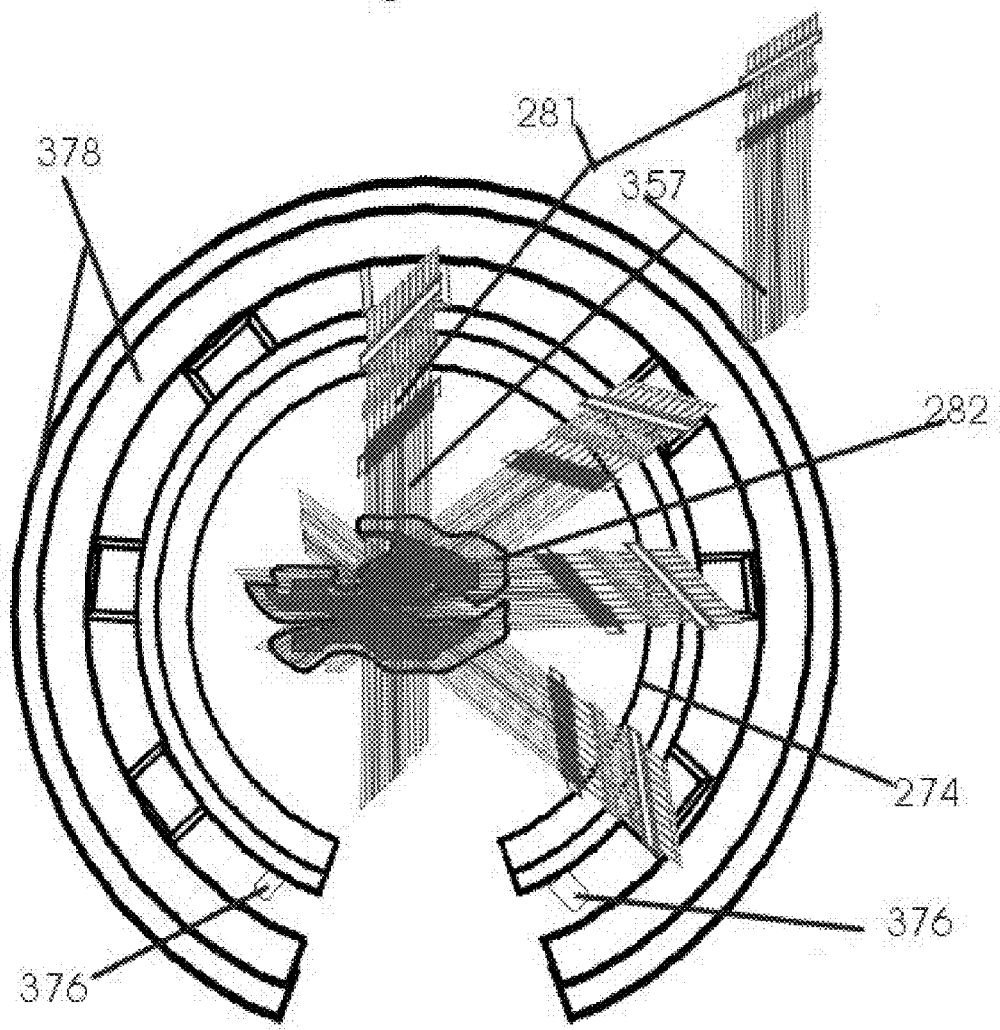

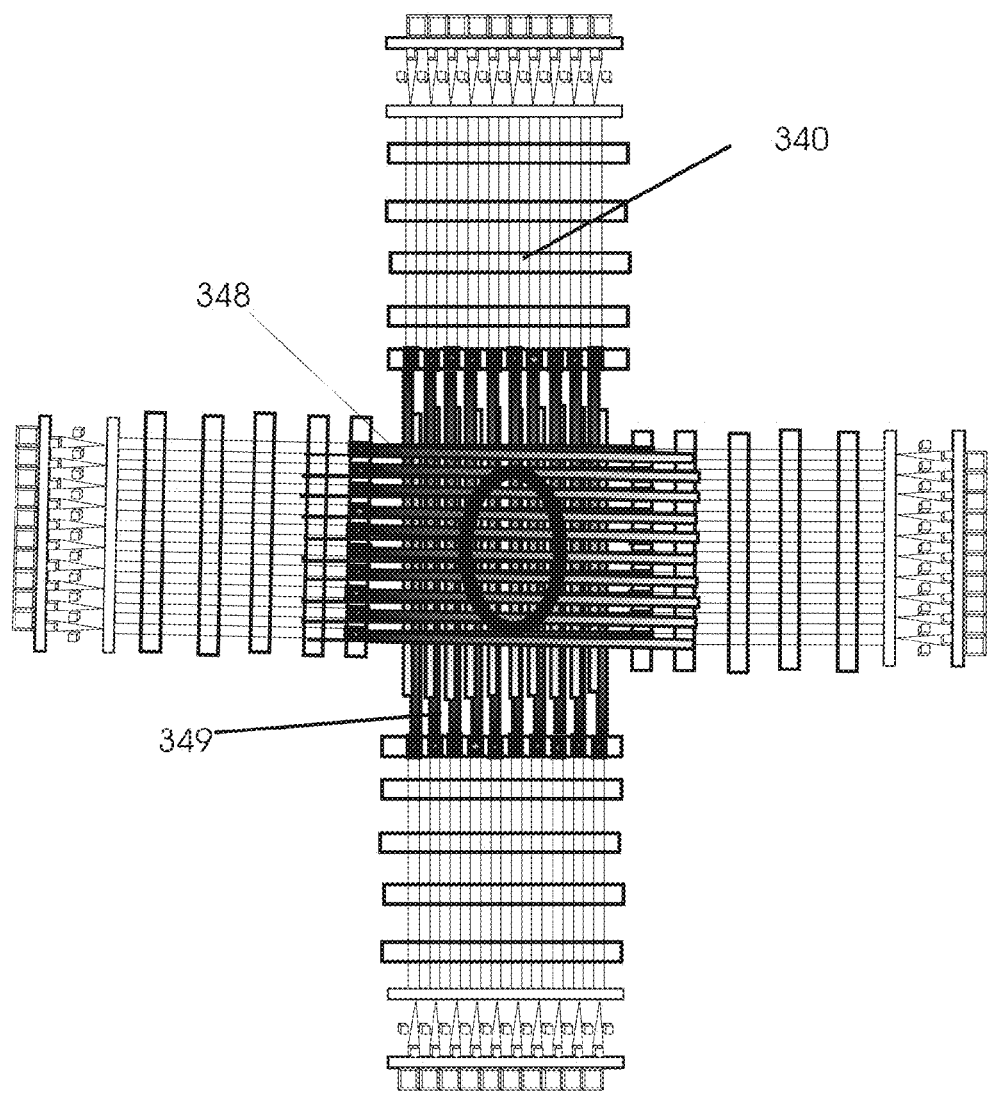

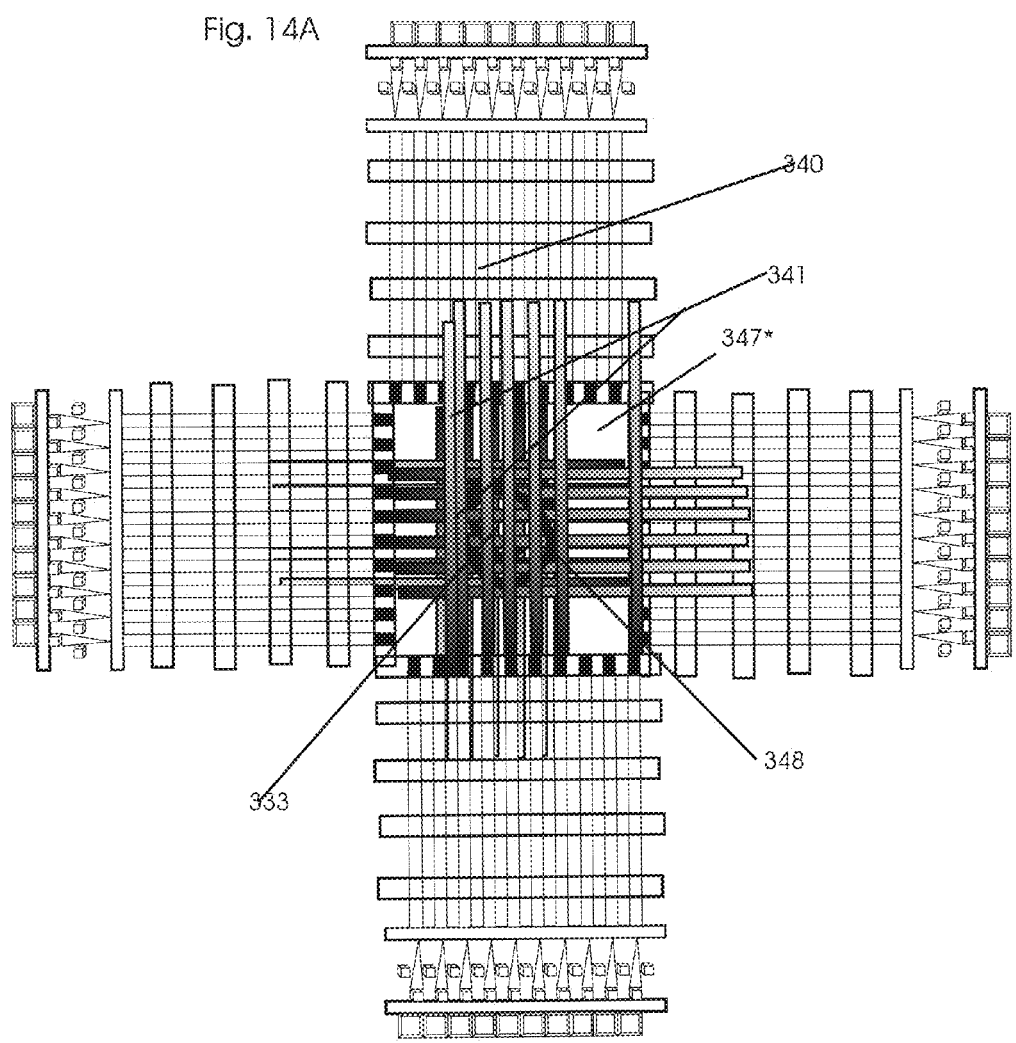

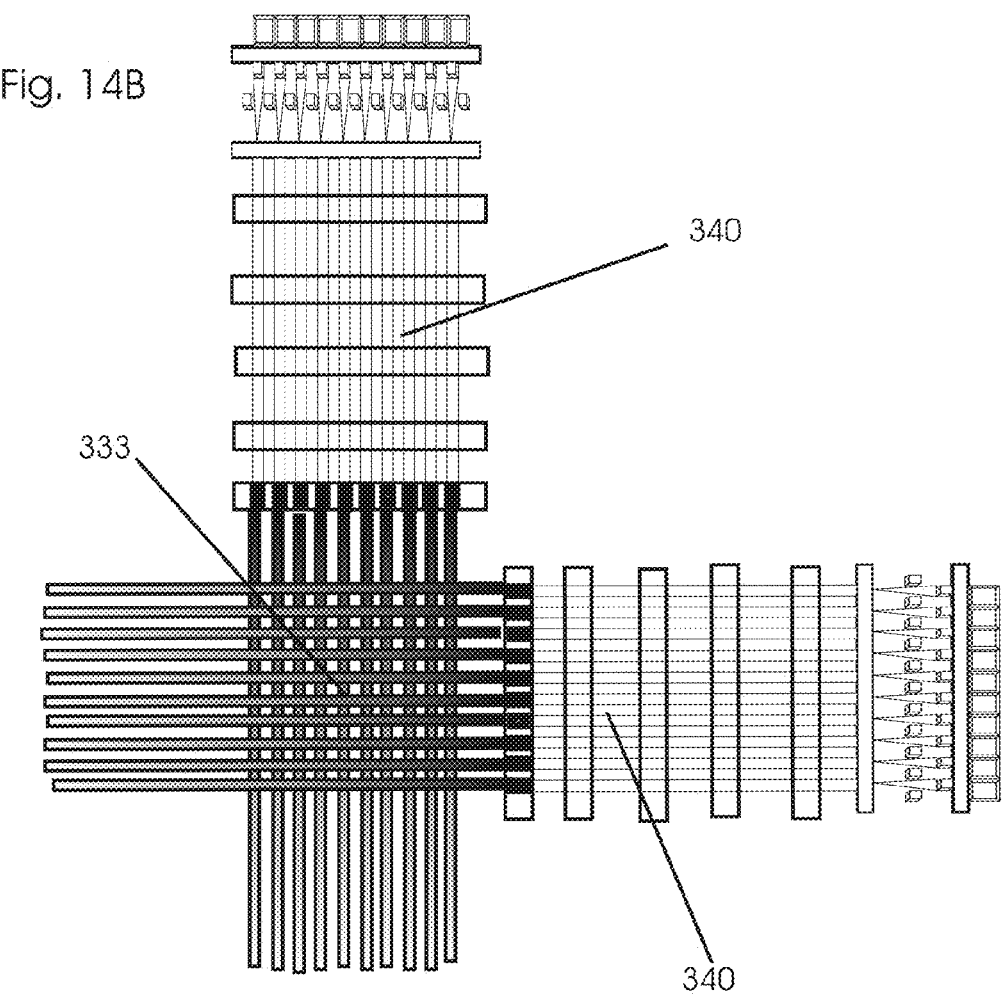

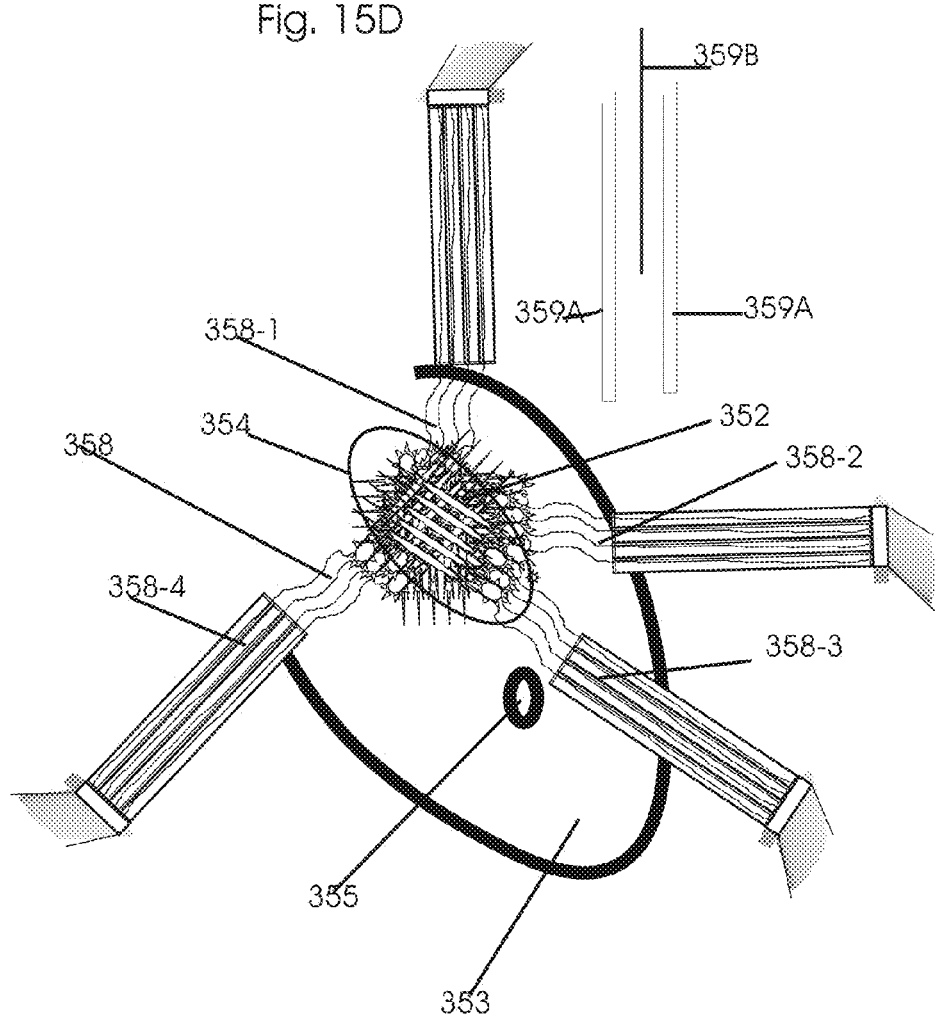

MEMS BASED PARALLEL MICROBEAM RADIOSURGERY WITHOUT ADAPTIVE RESISTANCE TO RADIATION

The present nonprovisional application is a Continuation-In-Part of applicant's prior U.S. nonprovisional patent application entitled "Image Guided Intraoperative Simultaneous Several Ports Microbeam Radiation Therapy with Microfocus X-Ray Tubes", Ser. No. 12/929,770, filed Feb. 15, 2011, which is hereby incorporated by reference in its entirety.

BACKGROUND OF THE INVENTION

1. Field of Invention

This invention relates generally to apparatus consisting of micro-electro-mechanical systems (MEMS) based miniature X-ray tubes with metal oxide crystal doped cold emission cathodes and transmission anodes and its use in methods of microbeam brachytherapy without adaptive radioresistance by single fraction 100 to 1,000 Gy and higher dose radiation in few seconds without much toxicity to normal tissue. It ablates cancer stem cells of mesenchymal epithelial transformation (MET) and inhibits tumor recurrence and metastasis. It stimulates active local and systemic immunity to the cancer so treated.

2. Field Emission Cold Cathode Electron Emitters and Field Emission Arrays

A single tip of a filed emission cathode of 60 to 90 nm can generate current densities of $10^8$ A/cm$^2$. Such field emission cathodes arrays (FECA) are capable of generating current densities of 10 to 2400 A/cm$^2$ (1). The electron emission from the gated cathode can be controlled by very low gate voltages of less than 100 V. It allows modulating, addressing and controlling the emission spatially. The brightness of a single tip at 10 mA could be in the range of $10^{15}$ A/m$^2$-steradian) which is a factor of 100 to 1,000 times better than thermionic cathodes (1). They can be microfabricated using Spindt microfabrication methods using a wide range of materials including silicon, gallium arsenide, zirconium carbide, hafnium carbide, titanium, niobium, tungsten, lithium, diamond, carbon nanotubes. They are widely used in low current and low duty cycle field emission flat panel displays. It makes the miniature x-ray tubes containing FECAs as ideal choice for external beam, grenz ray and interstitial implant radiation therapy.

3. Conventional Carbon Nanotube (CNT) Field Emission X-Ray Tubes

The miniature CNT-field emission X-ray tubes differ much from the conventional thermionic X-ray tubes. Tubular carbon nanotubes in the CNT-X-ray tubes have CNTs with nanometers in diameter and lengths millions of times its diameter. They have sharp ends. Its length to diameter aspect ratio is of over 1,000 s. They are thousands of times thinner than a human hair. Their walls are composed of single layer carbon atoms. Their field emission properties and operation at very low voltage makes them the smallest electron guns. In contrast to thermionic cathodes, they operate at low temperature with stable field emission and high brightness. They have perfect thermal and chemical stability. Its beam current is dependent on gate and cathode voltage difference and its X-ray energy is dependent on cathode and anode voltage difference. Focusing electrodes are used to focus the CNT-cathode's field emission electron beam onto a transmission anode.

4. Metal Oxide Crystal Doped Carbon Nanotube Cathode

Metal oxide doped carbon nanotube provides the unique properties of carbon nanotube and the metal oxide. The metal oxide is deposited onto the CNT tube as a continuous coating or as single crystalline film of controlled thickness or as nano particles. The metal oxide is deposited on CNT by physical vapor deposition evaporation methods or by sputtering. Vertically aligned CNT with metal oxide sputtered as crystal at the top of the CNT tube (2) is an ideal pyroelectric crystal—CNT combination cathode for X-ray generation. Both have excellent electrical and thermal conductivity. By heating and cooling, both the pyroelectric crystals and CNT can generate much more kilovolt electrons than when they are used as separate electron generating cathode sources. When heated or cooled in a vacuum environment, they are polarized spontaneously which generates perpendicular electric filed at the top and bottom of the CNT-metal oxide crystal. By shaping the metal oxide crystal at the top of the CNT as sharp pyramidal shaped cones, the strength of this electric filed is further increased and the electron beam is emitted from sharp peak of the crystal. The electron beam is focused with focusing electrode. Methods of Spindt semiconductor tip processing is employed to microfabricate the field emitter (3). The focused electron beam strikes on to transmission anode and generates X-ray beam that is collimated into fine focused microbeam. This CNT-metal oxide X-ray tube generates high brightness X-rays. An array of millions of such CNT-metal oxide crystal X-ray tubes are microfabricated to make high brightness microbeam with dose rate closer to Synchrotrons as parallel microbeam generating micro accelerator for tissue implants or for table top attached miniature accelerators for coronal, sagittal and transverse simultaneous high brightness parallel microbeam radiosurgery.

5. Brachytherapy, its Biologically Effective Dose Rate (BED) and Disease Free Survival Brachytherapy is delivered by implanting gamma or beta emitting radioactive sources directly into a tumor. It has the advantage of sparing the normal tissue than the radiation therapy with high energy external beam which has to travel through the normal tissue to reach a deep seated tumor. In general there are three methods of brachytherapy, the low dose rate (LDR) brachytherapy, the high dose rate (HDR) brachytherapy and pulsed dose rate (PDR) brachytherapy. The generally used radioactive sources for LDR, HDR and PDR brachytherapy includes Radium, Cecium-137, Cobalt-60, Iridium-192, Gold-198, Iodine-125 and Palladium-103. While the HDR is the high dose rate brachytherapy, its dose rate is still too low to kill aggressive tumor cells, especially the cancer stem cells. Its low dose and dose rate is not sufficient to unmask the tumor antigens by radiation. The typical Iridium-192 based HDR's dose rate is 5-10 Gy/min (4) that is 0.0833 to 0.1667 Gy/sec, (8.333 to 16.66 cGy/sec). At this dose rate, HDR brachytherapy do not cure aggressive tumors like glioblastoma multiforme while it is curable by Synchrotron microbeam radiation with dose rate of 10-20,000 Gy/sec and dose in the range of 700-4,000 Gy (5). Most remote afterloading HDR units start with a nominal 10 Ci Iridium-192 source which has the half life of 73.8 days. When the source strength reaches about 3-4 Ci, it is replaced (4). As the source strength falls, the dose rate and thereby the BED also decrease. It results in reduced disease free survival of patients treated by Ir-192-HDR (3). Increasing the dose and dose rate of future brachytherapy close to that of Synchrotron microbeam radiation therapy will increase the disease free survival, cure and control of the tumors as with the cure of glioblastoma by such treatments (5). This invention is aimed at this goal.

6. 4Rs of Conventional High Dose Rate (HDR) Brachytherapy and Radiosurgery

The dose per fraction is one of the most important parameters of the therapeutic ratio with high dose rate radiation therapy. 100 to 1,000 Gy single fractions, few seconds duration microbeam BrachyNext inhibits the 4Rs of radiobiology. It hardly gives any chance for the radiated tumor cells to Repair its radiation damaged DNA, Redistribution in cell cycle, Repopulation, and Reoxygenation of hypoxic cells as in protracted, fractionated radiation therapy. Importance of residual cancer stem cells after treatments is recognized as the root cause of radiation therapy failures but with no solution in sight to resolve these basic 4Rs of radiobiology related cancer stem cell radioresistance (6). The 100 to 1,000 Gy single fraction microbeam radiation presented here hardly has any 4Rs 7. 4Rs Defying, Single Fraction 100 to 1,000 Gy Microbeam RT 100 to 1,000 Gy single fractions, few seconds duration microbeam BrachyNext inhibits the 4Rs of radiobiology. It hardly gives any chance for the radiated tumor cells Repair of DNA, Redistribution in cell cycle, Repopulation, and Reoxygenation of hypoxic cells as in protracted, fractionated radiation therapy. Importance of residual cancer stem cells after treatments is recognized as the root cause of radiation therapy failures but with no solution in sight to resolve these basic 4Rs of radiobiology (6). The 100 to 1,000 Gy single fraction microbeam radiation presented here hardly has any 4Rs 8. Adaptive Resistance to Radiation Low dose and low dose rate daily fractionated radiation therapy induce adaptive response to radiation injury (7, 8) The adaptive response to radiation is evoked by a host of molecular events triggered by the oxidative process of ionizing radiation. Mouse skin pre-exposed to 10 cGy X-rays cause radioresistance to subsequent 200 cGy radiation. This adaptive resistance is mediated by the NF-kB family of proteins, the manganese superoxide dismutase, phosphorylated kinases, Cyclin B 1(9) and a number of other enzymes. More frequent HER2 positive invasive recurrent breast tumors occur after radiation as compared to primary tumors (10). Peptic ulcer treated with radiation to a dose of 1500 to 2000 cGy by orthovoltage radiation is known to increase the risk of gastric cancer. When this radiation was combined with surgery, it increased 10 fold. (11).

9. Adaptive Radiation Resistance to Fractionated Radiation Therapy

NF-kB activation and radio and chemoresistance are noted in breast cancer. HER2-(Human Epidermal Growth Factor Receptor 2) in breast cancer is known to cause aggressive tumor growth. HER2 expression can be induced by radiation in breast cancer cell lines with low basal level of HER2. The NF-KB is required for HER2 activation by radiation and the HER2 and the NF-KB are co-activated by radiation. NF-kB mediated HER-2 over expression is reported in adaptive radioresistance in breast cancer (10). HER2 mediated radioresistance is inhibited by siRNA (10). The fractionated ionizing radiation therapy at 4 Gy fractions to 60 Gy total dose to human small cell lung cancer lines induced 59 upregulated genes that were associated with DNA damage repair and 43 down regulated genes. The up-regulated genes were associated with DNA damage repair, extracellular matrix, cell adhesion and apoptosis and the 43 down regulated genes were associated with angiogenesis, immune response and calcium signaling pathways (12). The truncated epidermal growth factor receptor EGFRvIII and EGFR wild type (EGFRwt) are co-expressed in human carcinomas and glioblastoma when they are grown as xenografts but not when they are grown in vitro. A single 2 Gy radiation increased the Tyr phosphorylation 2.8 times in EGFRwt (wt-wild type). In EGFRvIII it was increased 4.3 fold. The pro-proliferative mitogen activated protein kinase in EGFRvIII was increased to 8.5 folds. Likewise, the antiapoptotic AKT/phosphatidylinositol-3-kinase pathways in EGFRvIII were increased to 3.2 folds (13). EGFRvIII is known to be a major factor in the radioresistance in glioblastoma multiforme brain tumors (14). Like EGFRvIII, Akt might be an important gene that induces increased radiation resistance in glioblastoma multiforme (15).

10. EGFR as an Example of Adaptive Radioresistance in Clinical Practice

Adaptive radiation resistance is the cellular response to irradiative stress. It is expressed in the cells that survive the very first fraction of the usual total 30 to 40 fractionated radiation therapy. It's EGFR and TGF-α is upregulated. Within 5 to 10 min after the very first dose of 1 to 5 Gy radiations there is a 2-5 fold increase in tyrosine phosphorylation. It returns to base level value within 5-10 min. (16). Such phosphorylation after the very first fractionated dose of radiation is found only in EGFR expressing tumors. Thus it is an adaptive radiation resistance resulting from the first dose of a conventional fractionated radiation therapy regime. Hence it is an acquired or an activated radioresistance. Several EGFR inhibitors are used to overcome this adaptive radioresistance. They include cetuximab, TKIs, antisense nucleotides, other antibodies like hR3 and panatumumab. The radiation therapy combined with these agents increase the tumor response but they also become ineffective acquired adaptive drug resistance. (16). Hence, these inhibitors are effective only for a very short time and afterwards, the tumor re-grows more aggressively.

11. Adaptive resistance to Radiation Inhibiting 100 to 1,000 Gy and higher dose Radiosurgery Conventional fractionated radiation therapy can induce radiation resistance. While radioresistance inhibiting cancer drugs could minimize the radioresistance, adaptive resistance to such drugs makes them also less effective soon after its first or second use. Inducing HER-2 positive breast tumor recurrence in patients whose initial tumors were HER-2 negative by fractionated radiation therapy (10) and its long term consequences to the patient is of grave concern. By single fraction, 100 to 1,000 Gy and higher dose radiosurgery with no or minimal normal tissue toxicity sterilizes the tumor, induces local and systemic immunity to the cancer so treated and it eliminates the clinical consequences of adaptive resistance to radiation.

12. Exposure of Tumor Antigens by 100 to 1,000 Gy and Higher Dose Brachytherapy and Induction of Regional and Systemic Immunity Against the Radiated Tumor Gp96 bound to the cell membrane of the antigen processing cells induce major histocompatibility complex (MHC) specific cytokines secretion. The specificity is derived from histocompatibility class 1 restricted crosspresentation of Gp96 associated peptides. Gp96 stimulates the secretion of proinflammatory cytokines from macrophages and dendritic cells.

Antigen from damaged, proapoptotic and necrotic cells are processed as major histocompatibility complex (MHC) class 1 antigen by the dendritic cells. The activated dendritic cells stimulate the CD8 T-lymphocytes in vitro and in vivo (17). Like the Gp96 binding proinflammatory stimulus from infection and tissue necrosis, radiation cause inflammatory stimulus. Irradiated cancer cells like those from prostate cancer can activate dendritic cells (18). Dendritic cells phagocytosed antigen migrates to lymph nodes and interacts with varying subsets of T-lymphocytes. Dendritic cells capture killed cells containing tumor specific antigens and produce tumor specific immunity. Intact cancer cell like that from prostate cancer is not processed by the dendritic cells (17). On the other hand, radiation damaged cancer cells is captured by the dendritic cells and brought to the lymph nodes to produce tumor specific immunity by the T-lymphocytes in the lymph nodes (17). The immune tolerance to cancer cells is mediated by masked tumor antigen. This masked tumor antigen is unmasked in cancer cells that are severely damaged and unable to replicate; that is in effect they are killed. Unmasked tumor specific antigen and its tumor specific fingerprint peptides is taken up and chaperoned by the heat-shock protein Gp96 and delivered to the dendritic cell. Dendritic cells transport it to the lymph nodes. In the lymph nodes this tumor specific antigen-peptides is taken up and initiates tumor specific immune response in CD4 and CD8 T-lymphocytes (17,19). In clinical practice, the heat-shock protein Gp96 is associated with radioresistance. For patients with head and neck tumors receiving radiation therapy, it is identified as an adverse prognostic factor (20). During the course of daily low dose, 1.8 to 2 Gy radiotherapy to a total dose of 60-80 Gy in 8-10 weeks, the tumor acquires adaptive resistance to radiation. In tissue culture experiments with, single fraction doses of as high as 25 Gy was ineffective to suppress the CaSki and H-3 cervical cancer cells proliferation completely while higher single fraction doses of 50 and 100 Gy could completely inhibit the proliferation of both these CaSki and H-3 cervical cancer cells (21). Like the highly radioresistant CaSki and H-3 cervical cancer cell, the radioresistant head and neck tumors also needs very high single fraction dose to stop its proliferation completely. Hence, the daily dose of 1.8 to 2 Gys fractioned radiotherapy to a total dose of 80 Gy in 6 to 8 weeks will not sterilize the entire head and neck tumor cancer cells. Only dead or dying cells are processed by the dendritic cells that elicit immunity against cancer (17). In response to radiation induced inflammatory reaction Gp96 heat-shock protein is produced. Higher the radiation dose, higher the concentration of Gp96 that is produced in response to radiation. Tumor cells radiated at relatively high dose of 25 Gy still had residual proliferating tumor cells. While this dose of 25 Gy irradiative stresses could produce Gp96, it was ineffective to elicit complete tumor specific immunity. However, tumor cells radiated with single fraction 50 G and 100 Gy kills the tumor cells completely. In this instance, there is also a dose dependent increased Gp96 (17). The dead cells are processed in the dendritic cells with the help of Gp96 that leads to cancer specific immunity. With completely killed cancer cells and increased Gp96 with 50 and 100 Gy radiations (17), more efficient tumor specific immunity is achieved.

A number of tissue stress injury can produce Gp96 heat-shock protein. They include heat, viral infections, hypoxia and oxidative stress like that caused by radiation. However, in the absence of complete killing of the cancer cells in a tumor, no efficient Gp96-dendritic cell can take place that could lead to complete immunity against cancer. Viral infection and hypoxia will not kill all the tumor cells in a tumor. Heat can kill the tumor cells but in clinical practice, it is impossible to apply sufficient heat to kill the entire tumor cells. Hence heat therapy alone is inefficient to induce lasting immunity against cancer. Radiation therapy is aimed kill all the tumor cells but the present clinical practice of daily 1.8 to 2 Gy fractionated radiation to a total dose of 60-80 Gy in 8-10 weeks is an inefficient radiation therapy to kill all the tumor cells, especially the cancer cells in a radioresistant tumor. The low dose and dose rate conventional LDR, "HDR" and PDR brachytherapy do not kill all the tumor cells including the cancer stem cells. Likewise, their dose is so much insufficient to expose the tumor specific antigens. Hence it is also ineffective to induce complete immunity against cancer by the Gp96-dendritic cell interaction. Safe single fraction very high dose radiation therapy, with doses in the range of 100 to 1,000 Gy and higher as described in this invention and those described with the aid of synchrotron based microbeam (22) on the other hand kills all the cancer cells in a tumor. With completely killed cancer cells in a tumor by microbeam radiotherapy, the Gp96-dendritic cell system interacts with the lymph nodes that elicit complete immunity against cancer.

13. Enhanced Monoclonal Antibody Binding to Tumor Antigens after External Beam Radiation as Evidence for Radiation Unmasked Tumor Antigens External beam radiation to a tumor cause several fold increased uptake of tumor antigen specific, radio labeled antibodies by the tumor. A four fold increase in monoclonal antibody uptake by the human xenografts colon carcinoma following 400 to 1,600 cGy external beam radiation is reported (22). Several methods for enhanced monoclonal antibody binding to tumor specific antigens has been tried, they include pre treatment of the tumor with radiation, interlueken-2, interferon and biologically active antibodies (23). Single dose 10 Gy radiation to human melanoma tumors transplanted subcutaneously into nude mice increase the tumor specific uptake of Indium-111 labeled anti-p97 monoclonal antibodies in this tumor (24)). Previously, this increased antibody binding to tumor specific antigens was thought to be due to radiation induced vascular permeability of the tumor. However there are other cellular mechanisms that cause increased antibody binding to tumor after radiation. They include radiation induced cancer cell's adaptive response, apoptosis and cell death and the exposure of the tumor specific antigens, especially through the FAS/FAS adaptive response that leads to increased tumor specific antibody binding to tumor. It seems to be the leading reason for increased antibody uptake by the tumor after radiation; not just due to increased vascular permeability.

14. FAS/FAS Ligand Death Pathway Tumor Specific Antigen and Cytokines Exposure by High Dose Radiation and its Tumor Specific Antibody Binding Hundreds to several thousands Gy, high dose localized radiation to a tumor in split seconds cause radiation induced inflammation at the tumor site. It releases a number of cytokines (25) and free radicals. Radiation evokes adaptive immunity through the FAS pathway (26). As described before, in vitro experiments, MC 38 adenocarcinoma cells at 20 Gy dose had increased FAS activity at molecular, phenotypic and functional levels. At this relatively higher dose radiation for an in vitro experiment, radiation sensitized these cells to antigen specific cytotoxic-T-lymphocyte's (CTLs) cell killing by FAS/FAS ligand pathway (27). In vivo experiments, the same MC 38 adenocarcinoma cells growing subcutaneously also showed 8 Gy radiation sensitized CTL adaptive immunity by up regulation of FAS leading to tumor growth arrest and tumor rejection (27). Gp96 mediated antigen-peptide processing with dendritic cells interaction are stimulated by radiated highly malignant prostate cancer cell line RM-1 but with higher dose radiation, in the range of 10-60 Gy which is relatively high single fraction dose for in-vitro experiments while unirradiated cells had no such immunostimulatory effects (18). Radiation releases several cytokines including IFN-γ which modulates tumor vasculature microenvironment and promotes the cytotoxic T-lymphocytes (CTLs) trafficking and its recognition by the tumor cells (28). The localized radiation dose to the mice in the experiments was 15 Gy (29) which is a large dose to treat a tumor in mice indicating the effectiveness of high dose radiation to modulate tumor immunity. It is increased with high dose and dose rate nanobeams and microbeams radiation. The interlaced multiple simultaneous microbeam and nanobeam radiation to the tumor as it is in this invention causes strong inflammatory reaction at the tumor site. The cytokines and tumor specific antigens exposed from the tumor and its FAS/FAS death pathways and apoptosis associated molecules effects the increased uptake of tumor specific antibodies after high dose radiation.

15. Heat-Schlock Protein Gp96 Immunotargeting Tumor Specific Immunotherapy, Immunoscintigraphy and Tumor Vaccines after Nanobeam and Microbeam Radiosurgery Heat-shock proteins are produced under stress including radiation. Heat-shock protein peptide complex prepared from tumor is capable of inducing immunity across a number of tumor types. It is an ideal class of tumor and patient specific immunity generating proteins. Thus, without the need for identification of each of the immunogenic peptides in a tumor, Gp96 class of proteins induces immunity across the tumors. Heat-shock protein, Gp96 based vaccine, Vitespen, also known as Oncophage is made from individual patient's tumors. It is active against a number of tumor types including melanoma, pancreatic, gastric and colorectal cancers, myelogenous leukemia and non-Hodgkin's lymphomas (30). In phase III study, the Vitespen vaccine is reported as effective against the most difficult to treat cancer, the malignant melanoma, including its stage IV cases (31). However, the overall results with Gp96 based immunotherapy and cancer vaccines are not very impressive. Only a very few patients have complete or partial response to this immunotherapy and cancer vaccine. Hence it needs to be much improved.

External beam radiation to a tumor cause four fold increased uptake of tumor antigen specific, radio labeled antibodies into the tumor (21). Single dose 10 Gy radiation to human malignant melanoma transplanted into nude mice increase the tumor specific Indium-111 labeled anti-p97 monoclonal antibodies into the tumor (24). The radiation induced cancer cell's adaptive response, apoptosis and cell death, the FAS/FAS adaptive response of the radiated tumor, all leads to increased tumor specific antibody binding to tumor. This adaptive response of the radiated tumor for enhanced tumor uptake of tumor specific antibodies into the tumor is much enhanced by high dose and dose rate localized nanobeam and microbeam radiation that is delivered within seconds to milliseconds as described in this invention.

Administration of Gp96 based immunotherapy like that with Vitespen in this case enhances its tumor uptake several folds than when it is given without pre-radiation of the tumor. This uptake is especially very high with very high dose and dose rate radiation with microbeam and nanobeam as it is in this invention. Likewise it facilitates much more efficient diagnostic, tumor specific antigen-antibody bound immunoscintigraphy of the tumor than with conventional immunoscintigraphy without pretreatment of the tumor by high dose and dose rate radiation. Complementary immunoscintigraphy is used for diagnosis and follow up of tumors (32). Complementary immunoscintigraphy with tumor antigen and peptide specific Gp96 leads detection of tumors and helps to guide elective treatment options and follow up like the radioactive iodine is used for the treatment of thyroid cancers. Pretreatment of a tumor with high dose and dose rate radiation leaves the tumor antigens exposed. It helps to perform more efficient Immunoscintigraphy that guides dose, frequency and duration of immunotherapy with Gp96 heat-shock protein vaccine like the Vitespen.

16. Super High Dose Microbeam Brachytherapy Boost to Conventional External Beam Radiation with Metal Oxide Crystal Doped Cold Emission Cathode—MEMS Generally, about 36 Gy brachytherapy boost radiation is added to conventional photon external beam radiation therapy. They still do not cure or control all the tumors. It still leaves substantial tumor cells behind that eventually cause local recurrence and distant metastasis. Super high dose and dose rate, 100 to 1,000 Gy and higher dose microbeam brachytherapy boost with metal oxide crystal doped cold emission cathode—MEMS to conventional external beam radiation on the other hand sterilize the cancer stem cells. It prevents and or minimizes tumor recurrence and distant metastasis. It also exposes the tumor antigens that induce local and systemic cancer immunity.

17. Phase Contrast Image Guided Parallel Microbeam Radiation Therapy

Computer assisted radiation therapy planning systems incorporates software tools for automatic contouring of tissue structures from absorption radiology's images. However, the absorption radiology imaging systems are incapable of soft tissue imaging; they are incapable of gathering detailed information on the tumor tissue since most of the tumor is made of soft tissue. To overcome this deficiency, the GTV, CTV, PTV and other important soft tissue structures are defined manually. Obviously, it is not very accurate.

Phase contrast imaging on the other hand is much different from the absorptive radiology. It is based upon the variations in phase structure that is made visible by phase shift of the x-ray photons. Minimal deviation from the initial path of the incident x-ray beam occurs as it interacts with the atom of the object that it radiates like when it pass through the soft tissue. Phase shift, also referred to as small angle scattering is a deflection of the incident beam within the object that it radiates. When the intensity of the deflection is large enough, the deflected x-ray is shifted to a different place, like to an adjacent pixel in the detector. Such phase contrast imaging is better suited to detect microscopic details in soft tissue. Any soft tissue structures that could produce deflection and from the incident photon's initial direction and its velocity is suitable for phase contrast imaging. Early soft tissue changes with increasing density such as in a very early developing cancer, inflammation associated changes in tissue all could induce measurable deflection of the incident monochromatic x-ray. The US patent application 20010038680 by Charles J Davidson, (33) and U.S. patent application Ser. No. 12/799,949 by Sahadevan (34) teaches the principles of phase contrast imaging and small angle phase shift of an incident monochromatic narrow beam in detail. It is referred here in its entirety. Phase contrast imaging is more suitable for soft tissue imaging that is composed of low molecular weight elements like carbon, oxygen, hydrogen, nitrogen etc. An array of low energy monochromatic X-ray microbeam that is used in this invention for intraoperative radiation therapy is highly suitable for phase contrast image guided radiation therapy. Similar phase contrast image guided radiation therapy is described in the patent application by this inventor (34).

More image details, especially the microscopic details is imaged by phase contrast imaging with low energy, longer wave length beams than it is possible with high energy, shorter wave length beams. Thus the 10 to 50 kV beams that are also used for intraoperative radiation therapy in this invention are capable of soft tissue imaging with its microscopic details. Phase contrast imaging is also used for clinical investigations that involve protein analysis, X-ray diffraction (XRD), single wavelength anomalous diffraction (SAD) phasing for protein analysis. The high brilliance microbeam generated with nanometer thick target and liquid metal alloy jet target are used for the phase contrast imaging in this invention. Liquid metal jet target is capable of generating 10 times higher brilliance than a microfocus X-ray tube's solid target (35). X-ray in-line phase contrast imaging (ILPCI) is used for noninvasive imaging of hepatocellular carcinomas at their different stages of developments (36). It needs no contrast agents. It differentiates both normal and tumor tissue, a significant advantage for image guided microbeam radiation therapy of this invention. The gray level co-occurrence matrix (GLCM) and dual tree complex wavelet transforms (DTCWT) in the phase contrast image is extracted to differentiate the normal tissue and the tumor tissue (35). Such noninvasive, micron level ILPCI also helps to visualize the tumor and its small vessels (35) that are associated rapid tumor proliferation as in tumors like the inflammatory carcinoma of the breast. It is very helpful for the follow up of differential radiation effects in tissue covered by the peak radiation path of the microbeam and in the normal tissue separating two adjacent microbeam paths, the valley region. Microbeam radiation therapy also spares the normal blood vessels while it destroys the proliferating micro tumor vessels; a basic difference between the normal tissue and the tumor tissue response to very high dose. It is one of the basic reasons for high microbeam radiation tolerance by the normal tissue while it ablates the tumor tissue (36, 37). Two arrays of microbeam, one from the lateral and the other as anterior-posterior and intersecting orthogonally at the tumor cause preferential damage to tumor micro vessels while preserving the radioresistant normal blood vessels (37).

Most of the tumor is made of soft tissue which is composed of low molecular weight elements like carbon, oxygen, hydrogen, nitrogen etc. Absorption radiology is incapable of soft tissue imaging. Phase contrast imaging on the other hand is more suitable for soft tissue imaging. Hence the present GTV, CTV, PTV and other important soft tissue structures as defined in computer assisted radiation therapy planning do not define the tumor margins composed of soft tissue precisely. Generally, the tumor margins with cancer stem cells are not visualized by the present conventional radiography, CT, MRI, PET and other methods of imaging. Hence other imaging method like those with near-infrared laser confocal endomicroscopy with indocyanine green is used to detect the infiltrative tumor growth margins (38). Like the mostly quasi monochromatic CNT and field emission crystal field emission x-ray (39), this invention's modified combined CNT- and crystal based X-ray generating MEMS also generates quasi monochromatic X-ray. It is further improved by elective target selection that produce Auger electron and characteristic monochromatic X-ray that is specific for the elected target element. It was also described by this inventor in previously issued patents (40). The cellular trace element analysis is based upon monochromatic Auger-electron characteristic-X-ray florescence analysis (41, 42). The micron and nano spot monochromatic x-ray beam with nearly no scatter improves the image quality 100 to 1000 times more than that for bremsstrahlung x-rays. It enhances the details in an image. Phase contrast imaging with quasi monochromatic X-ray microbeam visualizes the thick and complex soft tissue characteristics more precisely as 3-D images (43). The absorption radiography fails to visualize such details of a soft tissue tumor. Such phasecontrast imaging of the tumor combined with complementary metal oxide semiconductor (COMOS) based digital microscopy area scan sensor endoscopic image sensor camera (44) and MEMS based optical cancer imaging (45, 46) is combined with super high dose in situ image guided brachytherapy in this invention Like the in vivo, near-infrared laser confocal endomicroscopy with indocyanine green is used to detect the boundary of infiltrative tumor (47), these in situ image guided brachytherapy is used for precise determination of tumor volume and tumor margins for 100 to 1,000 Gy and higher super high dose brachytherapy in this invention.

18. Brief Summary of the Invention

MEMS based miniature X-ray accelerators with metal oxide crystal doped cold emission cathodes and transmission anodes and its use in methods of microbeam brachytherapy without adaptive radioresistance by single fraction 100 to 1,000 Gy and higher dose radiation in few seconds without much normal tissue toxicity as a means to control and cure tumors by ablating their cancer stem cells of mesenchymal epithelial transformation (MET) and to inhibit tumor recurrence and metastasis by induction of active local and systemic immunity to the cancer so treated.

This invention is on low-cost but advanced very high dose rate, 100 to 1,000 Gy single or fewer fraction multiple simultaneous X-ray microbeam radiation therapy delivery within a few seconds with Metal Oxide Crystal Doped Cold Emission Cathode—MEMS. It is aimed at control and cure of tumors by ablating their cancer stem cells of mesenchymal epithelial transformation (MET) origin by super high dose single fraction without much toxicity to normal tissue to inhibit tumor recurrence and metastasis. Its other goal is to induce local and systemic immunity to cancer by exposure of tumor antigens by super high dose radiation. Microbeam X-ray sources are placed as either external grenz ray sources or as interstitial seconds only duration implants. Metal Oxide Crystal Doped Cold Emission Cathode— MEMS based accelerators are used for radiation therapy and research in this invention. Multiple such MEMS-brachytherapy x-ray accelerators are brought close to surgically exposed tumor or to an organ which does not need such surgical exposure for contact radiation therapy. Multiple simultaneous beams are focused onto an isocentric tumor for additive high dose rate radiation therapy when it is by grenz ray contact radiation therapy. Multiple electronic brachytherapy X-ray accelerators are also used for simultaneous multiple port minimally invasive breast cancer treatment and for accelerated partial breast irradiation (APBI). MEMS microfabrication technology is used to construct the miniaturized grenz ray and interstitial accelerators. Its high dose rate is closer to that of synchrotron radiation. It is achieved with cathodes made of carbon nanotube doped with cold emission crystal and nanometer thick target or micrometer thick liquid metal alloy jet transmission anodes that has 10 times higher brilliance than a microfocus X-ray tube's solid target. It is combined with additive isocentric dose and dose rate of multiple simultaneous beams at the isocenter.

The CNT is packed with metal oxide to increase its conductivity. The metal oxide crystal is also loaded on top of the CNT. The electrical conductivity of these metal oxides loaded CNT that is also doped with metal oxide crystal at its top is several folds higher than CNTS without such metal oxide loadings. It increases further the dose and dose rate of CNT accelerators as compared to CNT accelerators without such metal oxide loading and doping.

Collimated orthogonal microbeam with 25-75 µm width and 200-400 µm spacing makes the peak and valley doses of the microbeam very distinct with 100% dose at the peak and about 10% dose at the valley region. The orthogonal microbeams intersect at the isocentric tumor where the characteristic scattered radiation fills in the radiation that gives homogenous radiation at the isocenter. The combination with monochromatic microbeam based phasecontrast imaging and radiation therapy further reduces normal tissue toxicity. It is also combined with characteristic auger transformation radiation from heavy elements that are implanted, injected or bound to tissue by high affinity binding by means of tissue specific receptors. The monochromatic beam's energy is tuned to the k, l, m, n shell binding energies of the tissue bound heavy atom nanoparticles. Such tissue specific radiation elicits the tumor specific radiation therapy. Radiation therapy is also rendered with external or interstitial monochromatic microbeams of 5 to 75 μm, preferably from 25 to 50 μm widths and close to parallel elongated beams. Such narrow width elongated monochromatic beams are used for treatment of both benign and malignant diseases and research. Its additive dose peak at the isocenter and the relatively very low dose at beam entry due to dose being distributed among a number of simultaneous beams from multiple ports and the sudden dose fall past the isocenter makes the dose distribution at the isocentric tumor very unique. Higher atomic weight iodine tagged ligands bound to the tumor or those that are implanted into the tumor such as gold or titanium or similar high z-element nanoparticles facilitates such Auger transformation radiation. Alternatively, for Auger transformation-radioimmunotherapy and gene targeted therapy the metallic nano particle bound monoclonal antibodies is administered directly into the tumor during the intraoperative radiation therapy. These combined locally absorbing Compton scattering and coherent scattering and the Auger transformation characteristic x-ray radiation have energies in the range of 10-20 kV. They enhance the RBE of the radiation within the isocentric tumor.

This invention's single fraction 100 to 1,000 Gy and higher dose radiation to a tumor within seconds is combined with phase contrast imaging which is more suitable for soft tissue imaging that is composed of low molecular weight elements like carbon, oxygen, hydrogen, nitrogen etc. It is also used for clinical investigations that involve protein analysis, X-ray diffraction (XRD), single wavelength anomalous diffraction (SAD) phasing for protein analysis. X-ray in-line phase contrast imaging (ILPCI) is used for image guised microbeam brachytherapy. It needs no contrast. It differentiates both normal and tumor tissue. Its micron level ILPCI is used to visualize the tumor and its small vessels.

Microbeam radiation spares the normal blood vessels while it destroys the proliferating micro tumor vessels; a basic difference between the normal tissue and the tumor tissue response to very high dose radiation. Two arrays of microbeam, one from the lateral and the other as anterior-posterior and intersecting orthogonally at the tumor cause preferential damage to tumor micro vessels while preserving the radioresistant normal blood vessels (37). Phase contrast imaging is more suitable for GTV, CTV, PTV and other important soft tissue structures imaging. Its image quality is 100 to 1000 times higher than imaging with bremsstrahlung x-rays. It is also combined with COMOS based digital microscope area scan sensor endoscopic image sensor camera and MEMS based optical cancer imaging.

19. Brief Description of the Drawings

FIG. 1 illustrates vertically aligned high aspects ratio single walled carbon nanotube 346 coated with metal oxide 350 in its interior and at metal oxide crystal 351 at its top and coated with parylene 352 at its exterior as cathode for high brightness parallel X-ray microbeam generation with dose rate close to synchrotron for microbeam radiosurgery.

FIG. 2 shows herringbone arrangement, stacked graphene carbon nanotubes 354 coated with metal oxide 350 in its interior and pyroelectric crystal parylene 352 in its exterior that generates high brightness parallel X-ray microbeam with dose rate close to synchrotron for microbeam radiosurgery.

FIG. 3A illustrates array of pyroelectric CNT-metal oxide crystal based parallel microbeam generating MEMS in which either single walled carbon nanotube is coated with metal oxide in its interior and pyroelectric crystal parylene in its exterior or with herringbone arrangement, stacked graphene carbon nanotubes coated with metal oxide in its interior and pyroelectric crystal parylene in its exterior as cathodes to make array of high brightness parallel microbeam with dose rate close to synchrotron for microbeam radiosurgery.

FIG. 3B shows an array of parallel microbeam generation with heating and cooling of pyroelectric crystal coated single walled carbon nanotube or herringbone arrangement, stacked graphene carbon nanotubes coated with metal oxide in its interior and pyroelectric crystal parylene in its exterior as cathodes to make array of high brightness parallel microbeam with dose rate close to synchrotron for microbeam radiosurgery.

FIG. 4 is a detailed illustration of the basic structures of a MEMS-X-ray tube based on single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior.

FIG. 6 shows a single set, 10-beam MEMS electron accelerator based on modified carbon nanotube field emission (mCNT-FE Accelerator).

FIG. 7C illustrates intraoperative parallel microbeam radiation to a tumor.

FIGS. 7D and 7E shows four sets of CNT based micro-accelerators 281 and their simultaneous 10 parallel microbeams 357 radiating a surgically exposed tumor.

Figure 8:
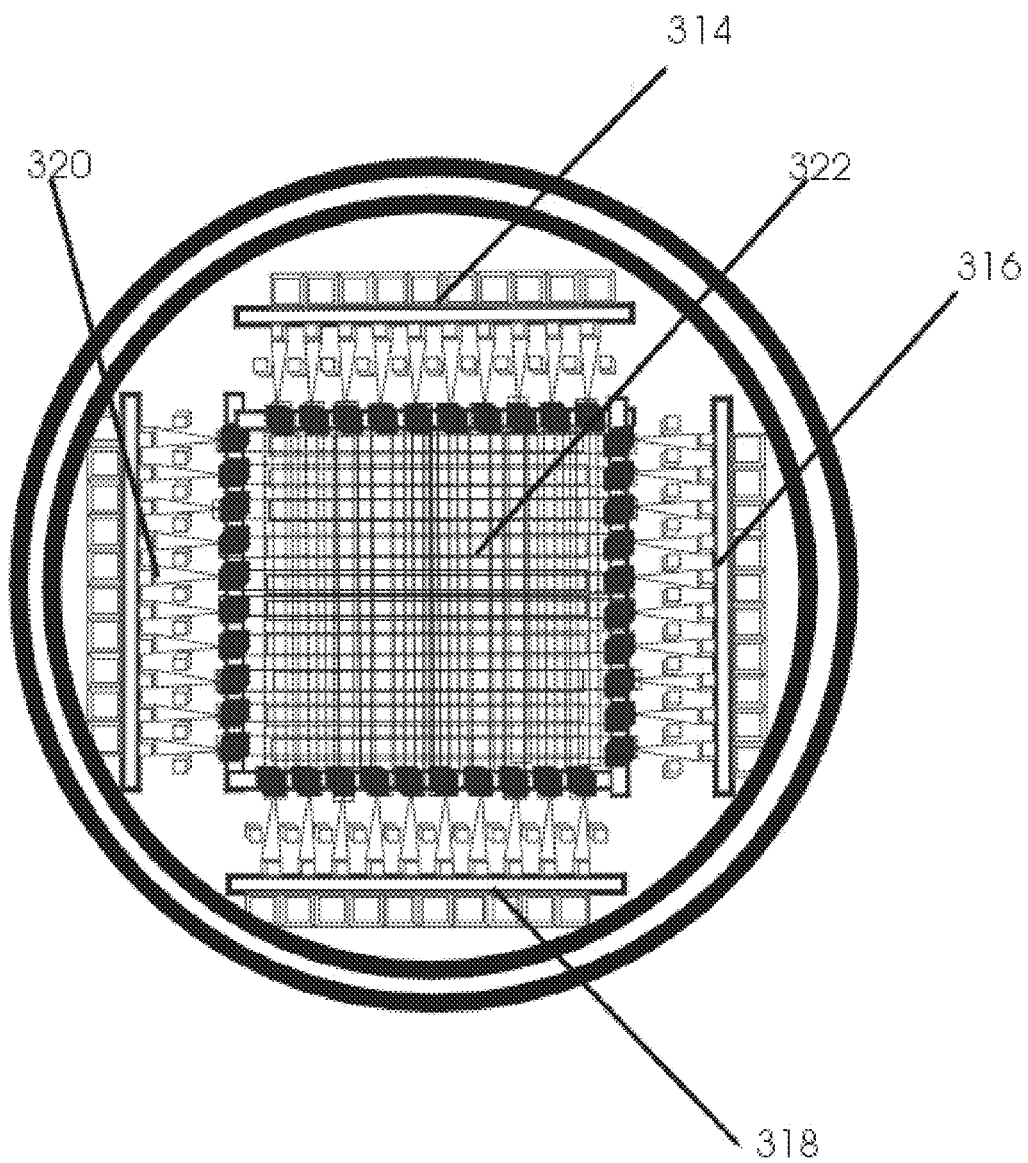

FIG. 8 illustrates four sets of CNT based X-ray tubes 312 with parallel microbeams arranged within a circle and each X-ray tube having 10 parallel microbeams, parallel microbeams X-ray tube with 10 beams from 0° 314, parallel microbeams X-ray tube with 10 beams from 90° 316, parallel microbeams X-ray tube with 10 beams from 180° 318.

Figure 9:
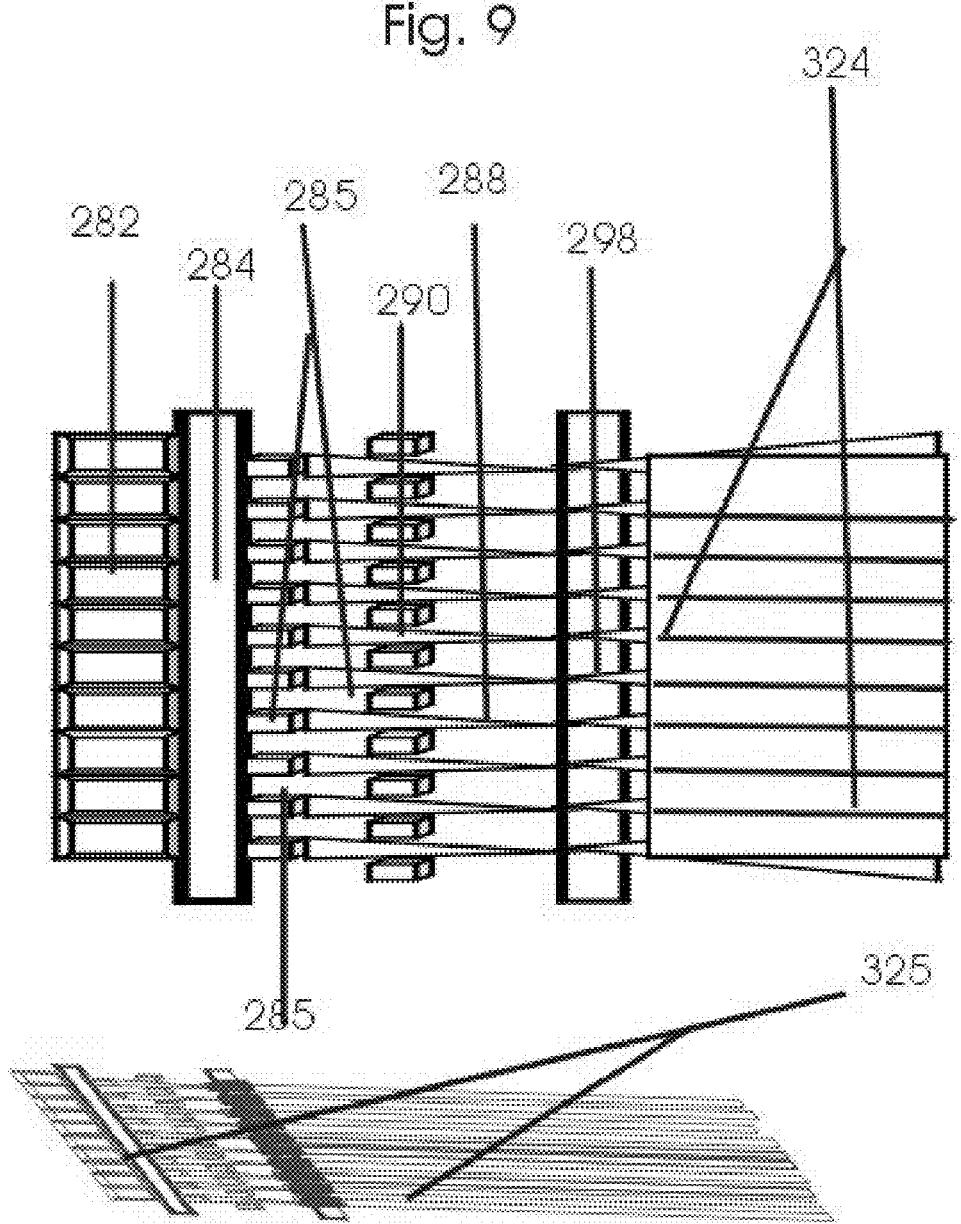

FIG. 9: As in FIG. 9 in the pending patent application Ser. No. 12/929,770, FIG. 9 in this Continuation-In-Part-Application shows a miniaturized interstitial implant with modified CNTs based X-ray tube and its basic structures.

Figure 10:
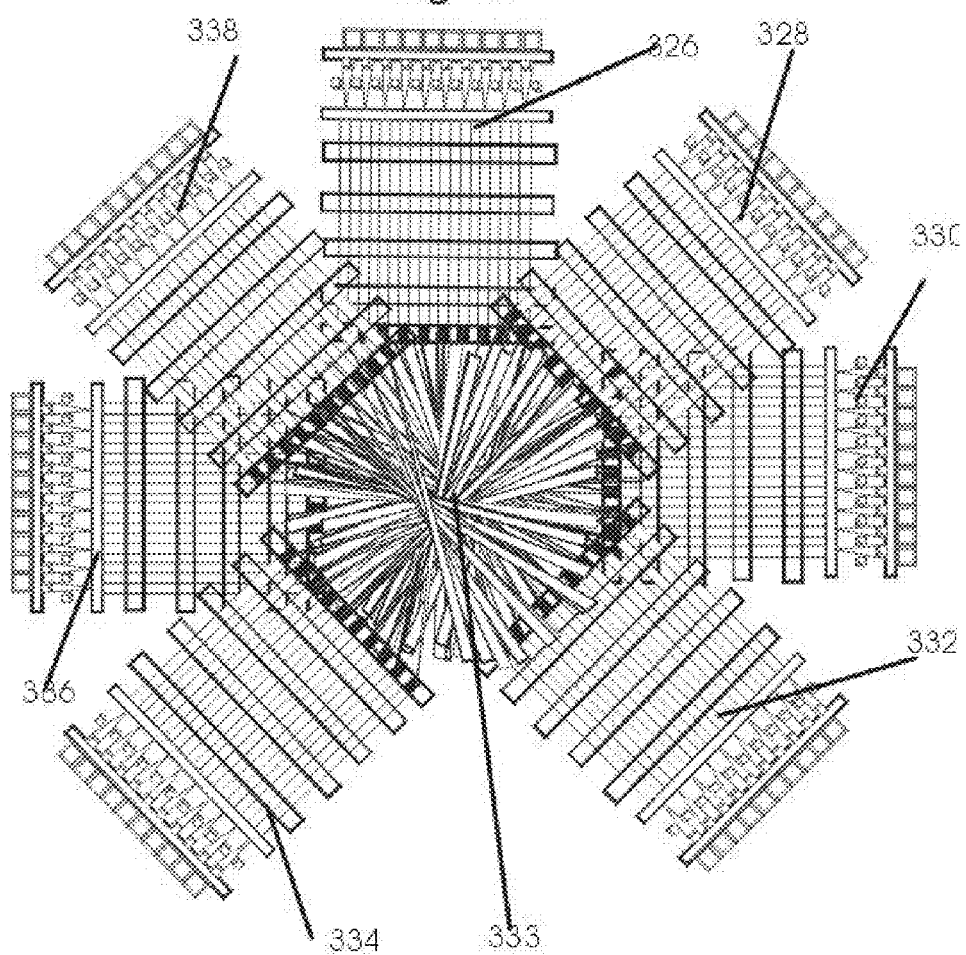

FIG. 10: As in FIG. 10 in the pending patent application Ser. No. 12/929,770, the FIG. 10 in this Continuation-In-Part-Application shows seven CNT based external electron accelerates with combined 70 microbeams that are passing through the isocenter and they intersect at the isocenter.

Figure 11:
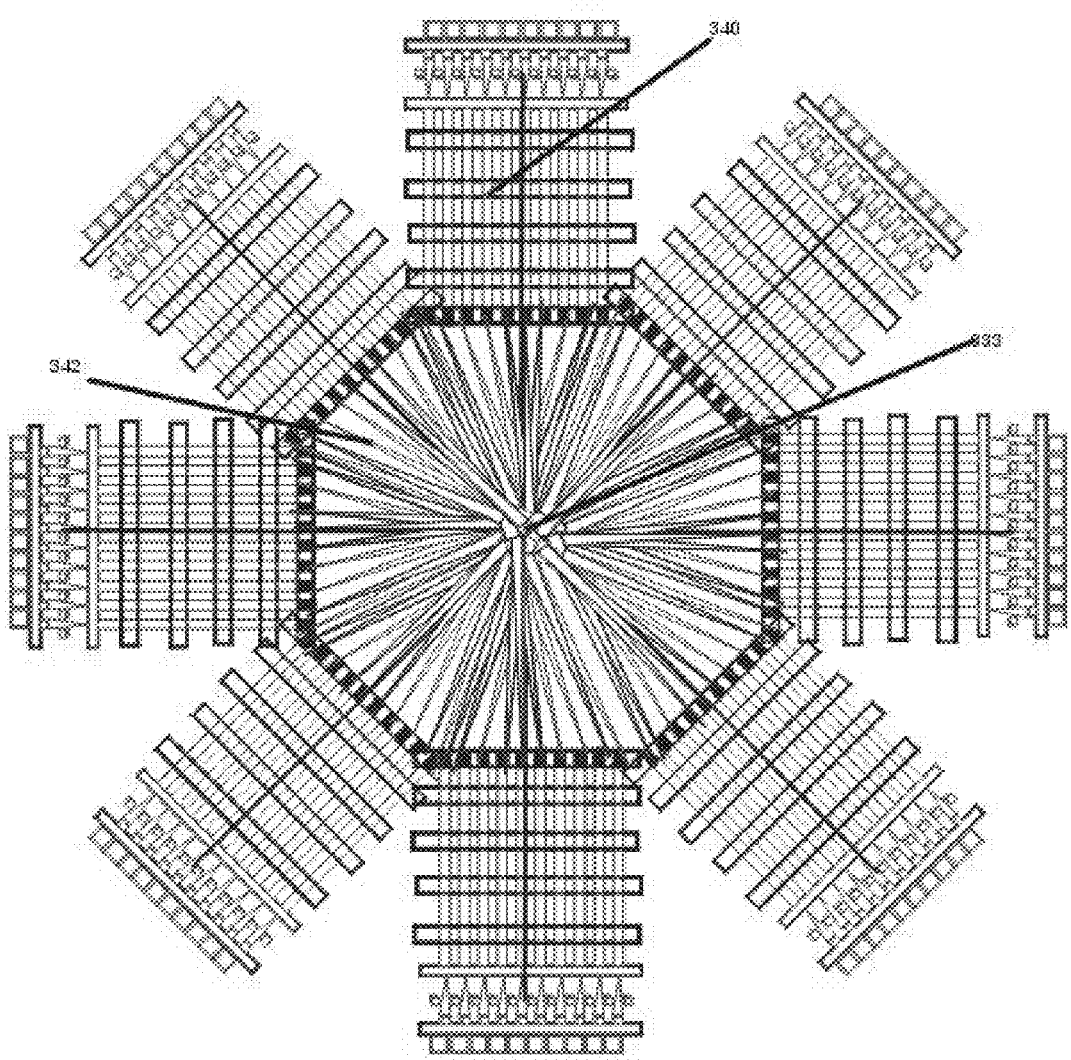

FIG. 11: As in FIG. 11 in the pending patent application Ser. No. 12/929,770, the FIG. 11 in this Continuation-In-Part-Application illustrates eight units of modified CNT based field emission accelerators, each with 10 parallel microbeams.

Figure 12:
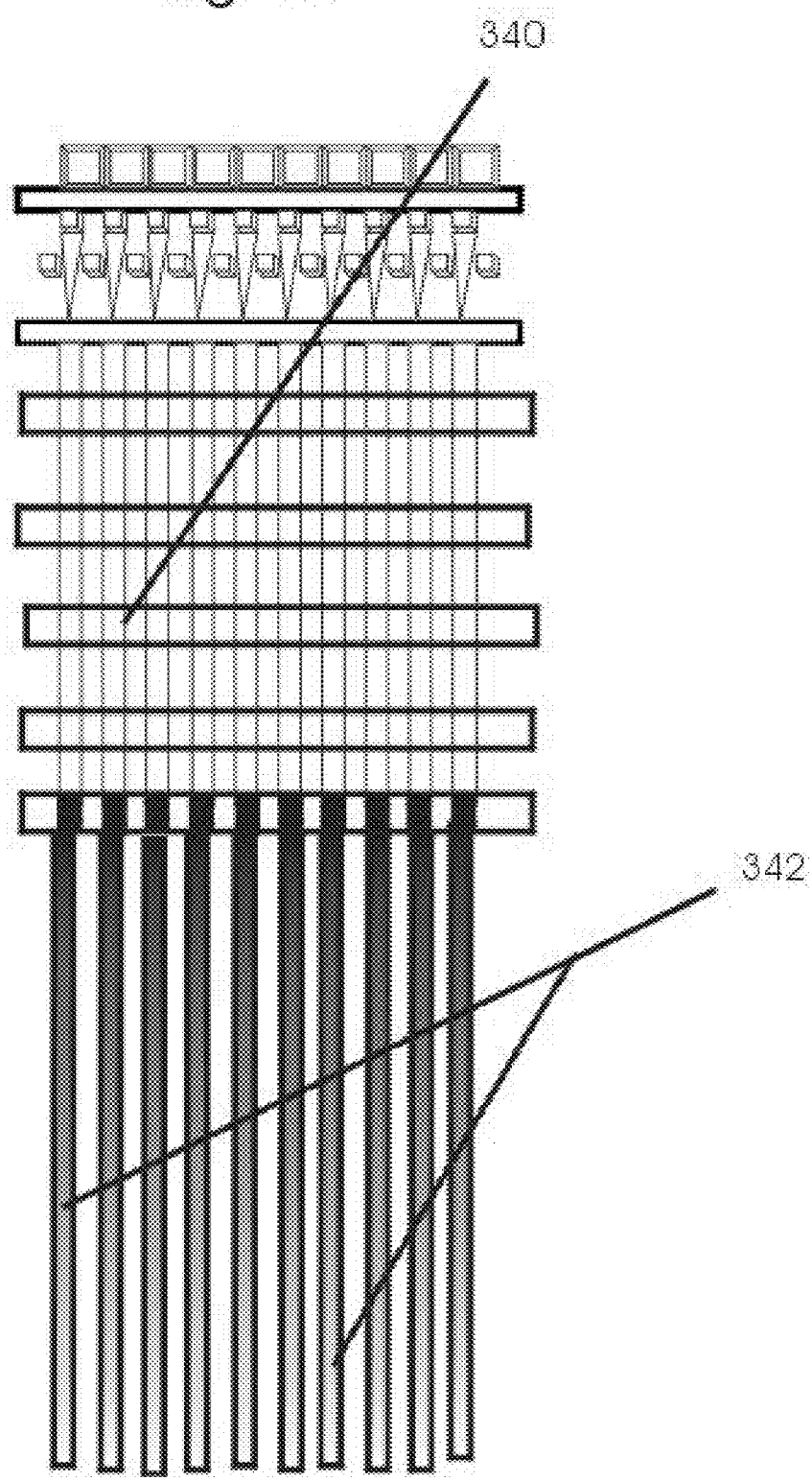
Figure 13A:
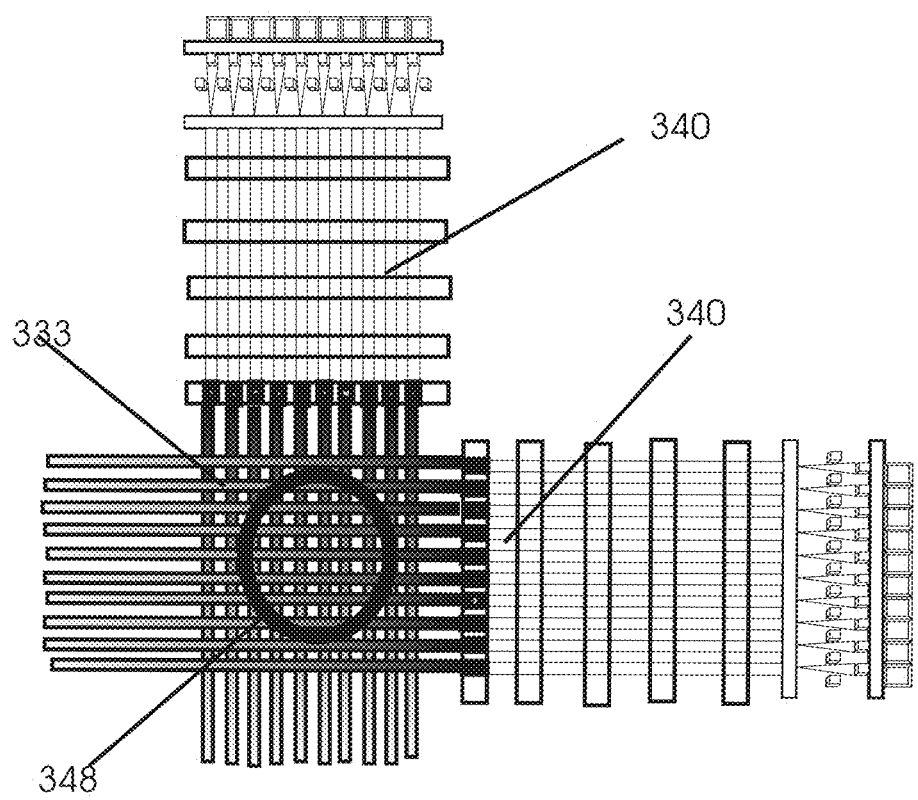

FIG. 12, FIG. 13A and FIG. 13B: As in FIG. 12, FIG. 13A and FIG. 13B in the pending patent application Ser. No. 12/929,770, the FIG. 12, FIG. 13A and FIG. 13B in these Continuation-In-Part-Application shows miniaturized 10 parallel beams accelerator for interstitial implant.

FIG. 14A: As in FIG. 14 in the pending patent application Ser. No. 12/929,770, the FIG. 14 in this Continuation-In-Part-Application shows selectively switched parallel opposing 6 simultaneous beams 341 from four sets of miniaturized CNT based 10 microbeams micro-accelerators 340 that covers the planning tumor volume 348 but with sparing of the isocentric region where no tumor is located.

FIG. 14B illustrates the parallel microbeams 342 from a set of miniature accelerators placed at 0 and 90 degrees. As these parallel microbeams intersecting at the isocenter 333, they do not overlap the normal tissue outside the isocenter 333.

Figure 15A:
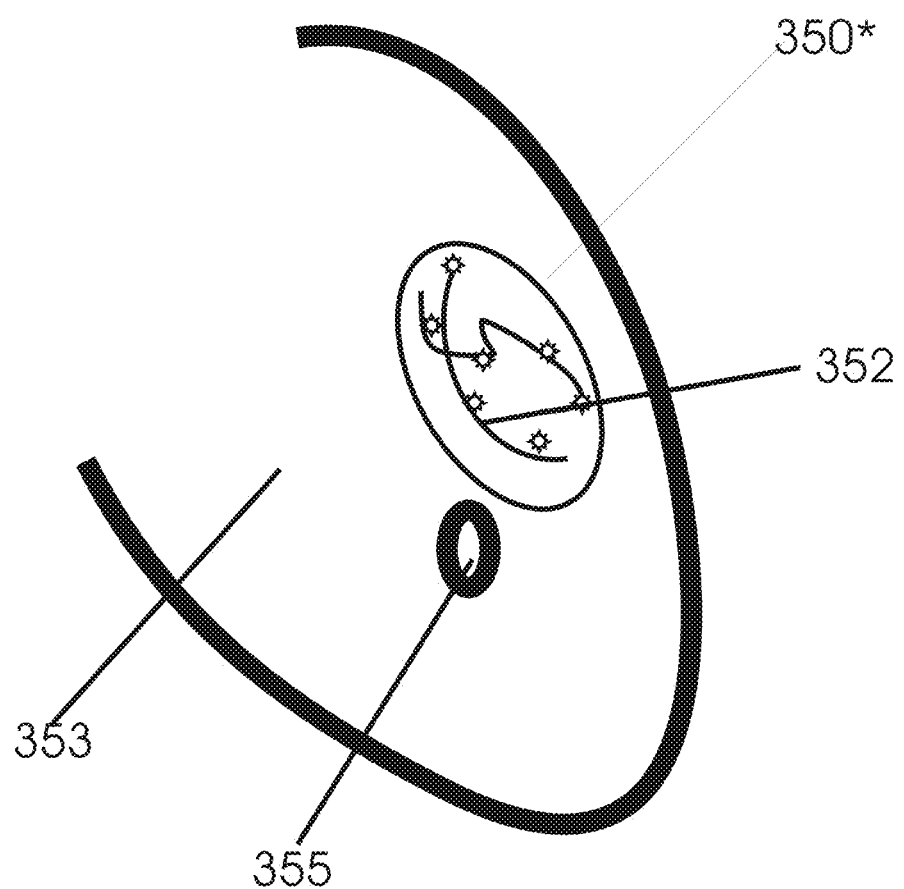

FIG. 15A shows an early stage breast cancer with microcalcifications

Figure 1:
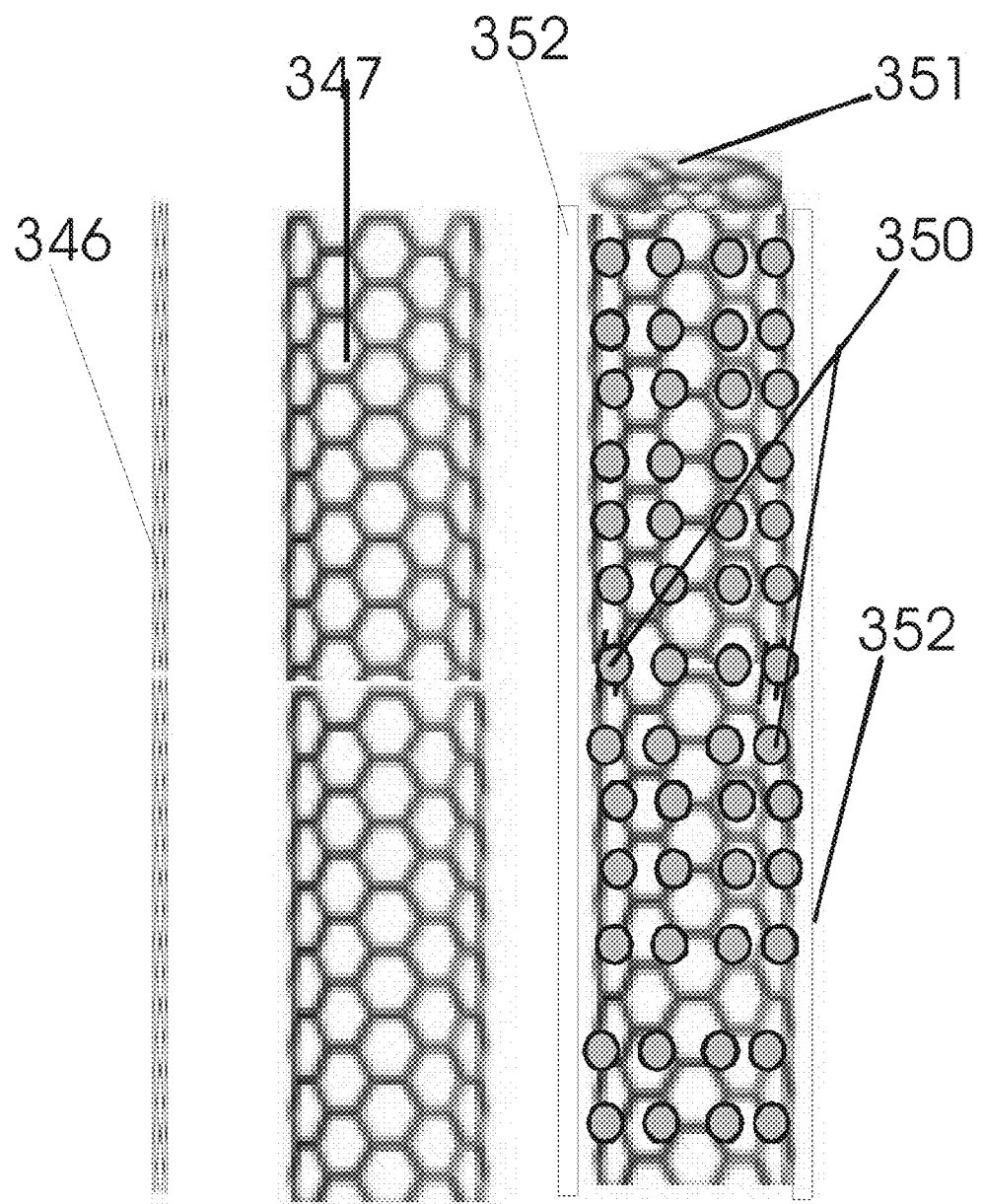
Figure 15B:
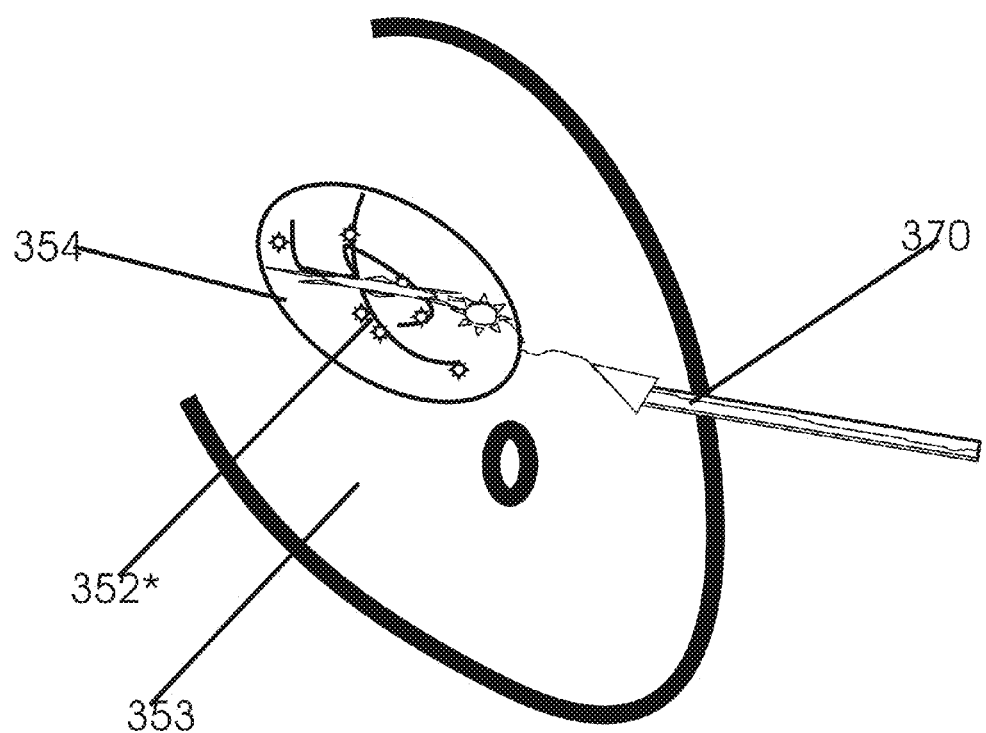
Figures 1, 15C:
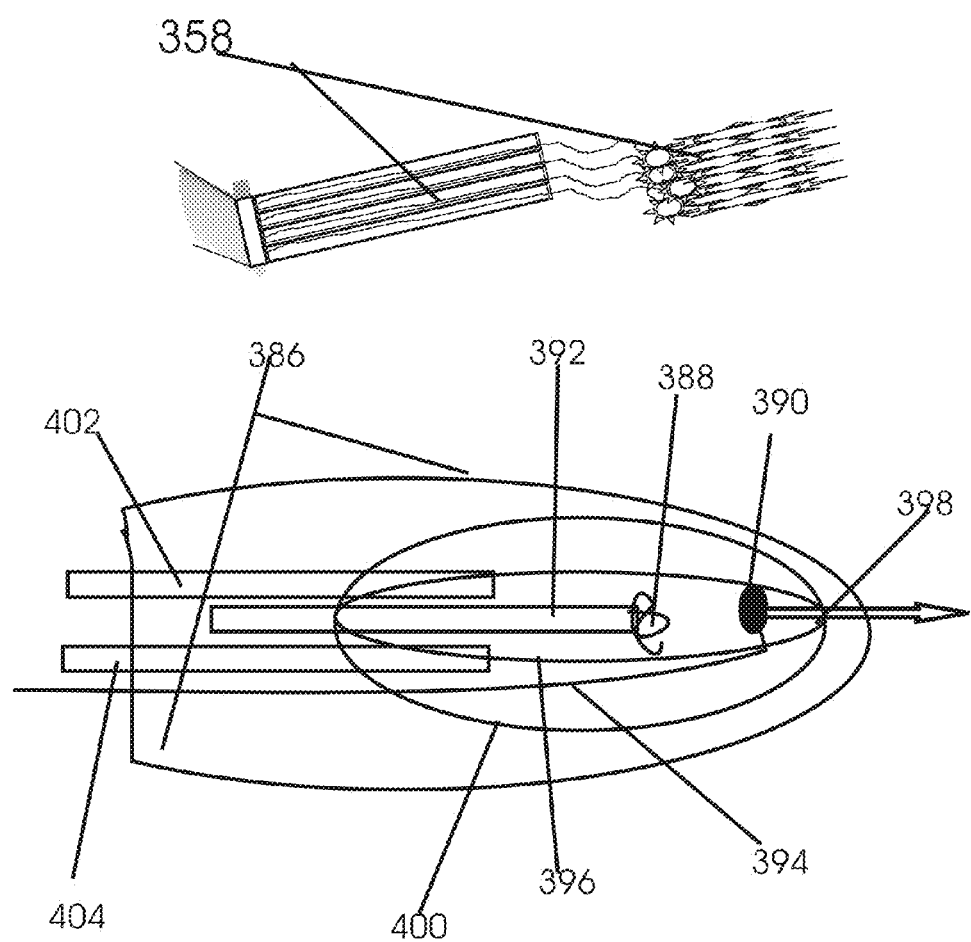
Figures 2, 15C:
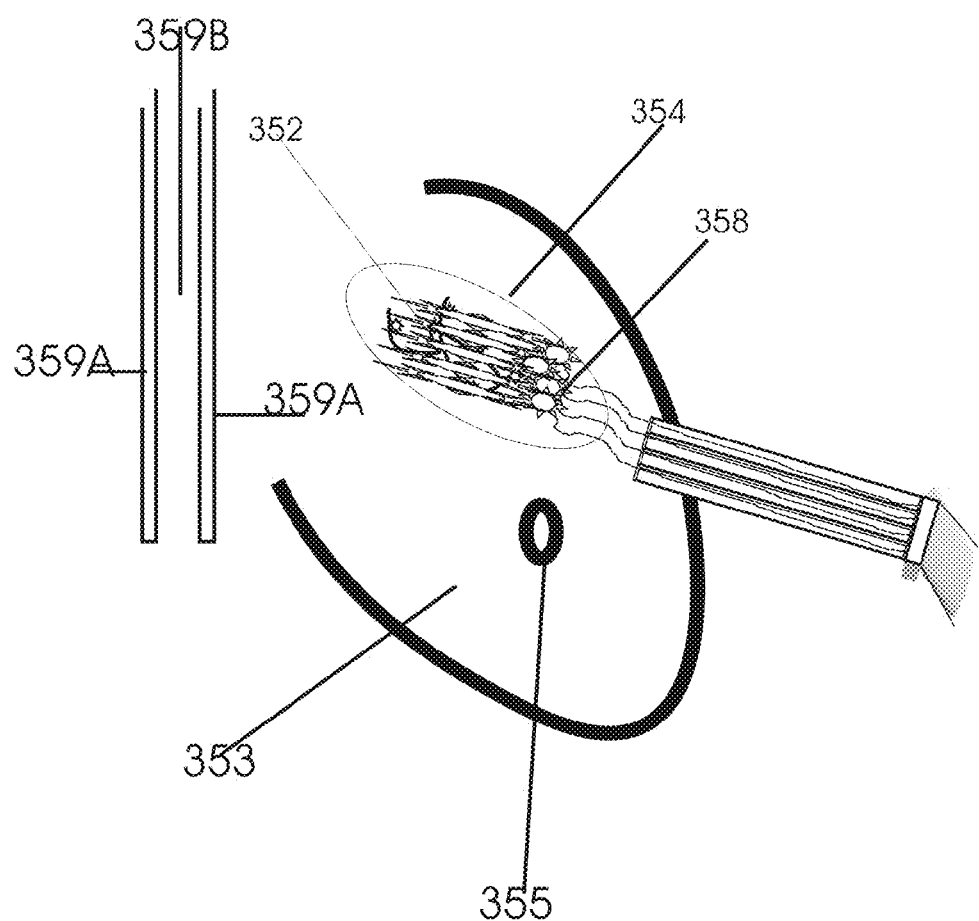
Figure 16:
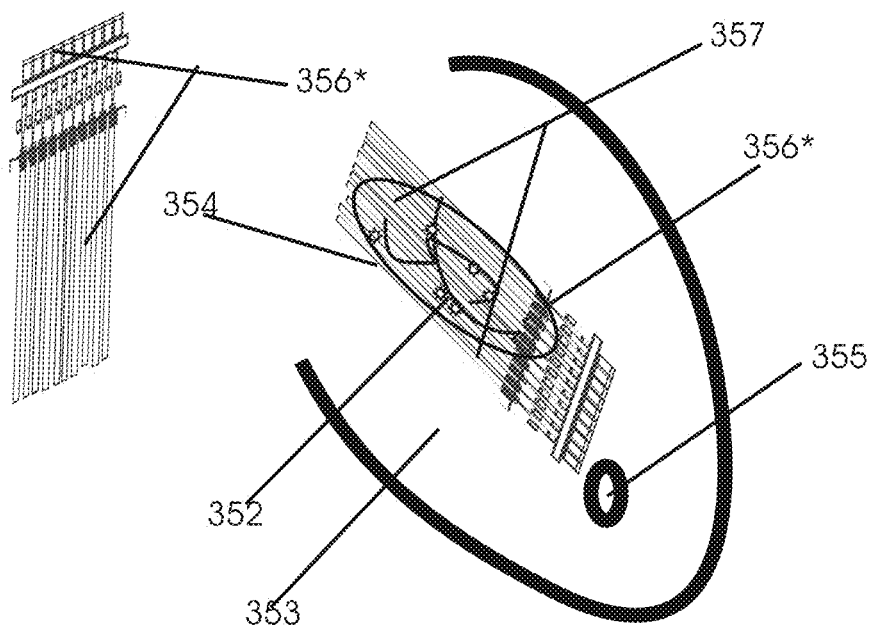

FIG. 15B shows an early stage breast cancer with microcalcifications treated with a single set electronic brachytherapy X-ray tubes FIG. 15C-1 is an illustration of a single micro X-ray tube assembly for implant FIG. 15C-2 shows an early stage breast cancer as treated with a single simultaneous four microbeam electronic brachytherapy system and the peak and valley doses FIG. 15D illustrates an early stage breast cancer treatment with four separate simultaneous four microbeam electronic brachytherapy systems FIG. 16 shows an early stage breast cancer as treated with a CNT based miniature interstitial implant with 10 parallel microbeams.

Figure 17:
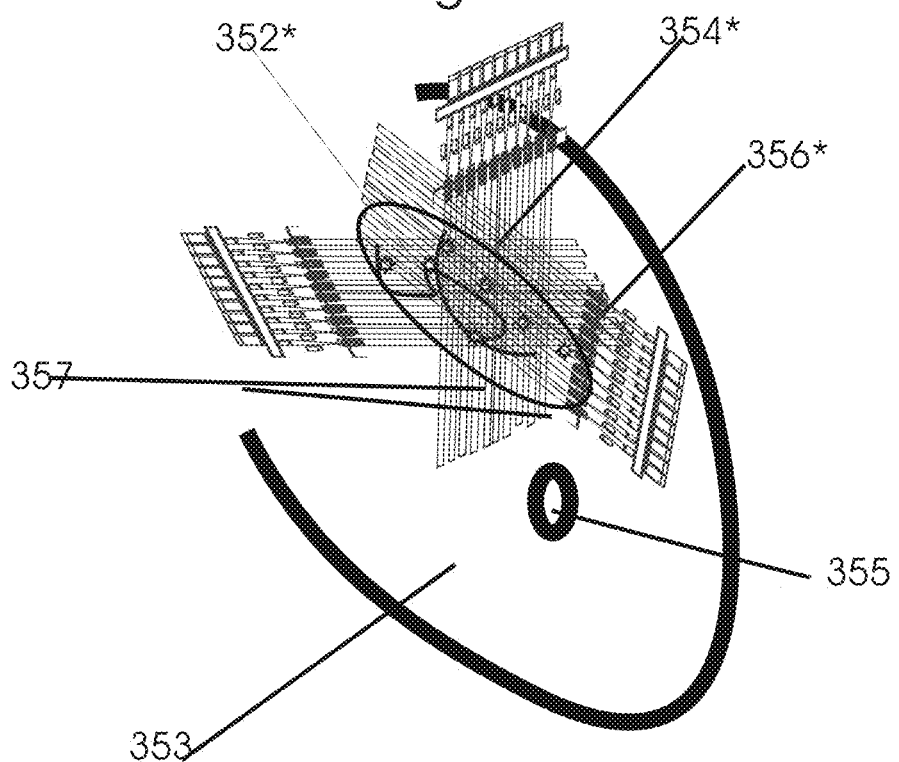

FIG. 17, illustrates treating an early stage breast cancer with 3 sets of CNT based miniature interstitial implants, each having 10 parallel microbeams.

Figure 18:
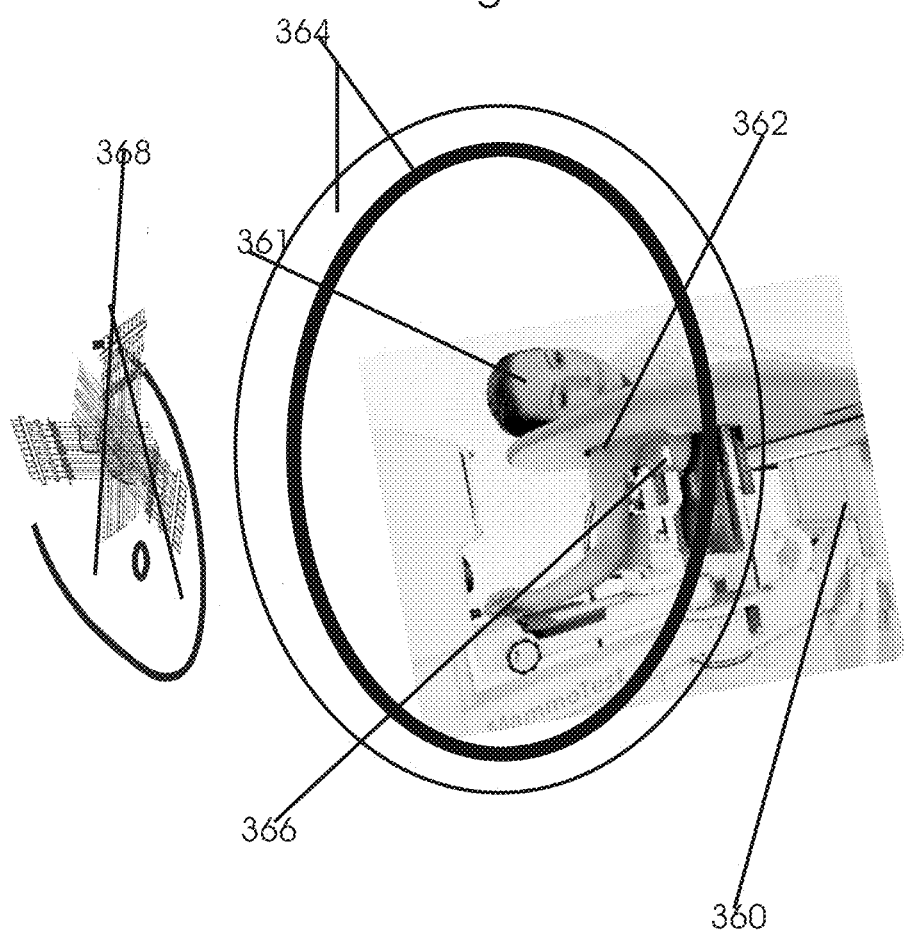

FIG. 18: As in FIG. 18 in the pending patent application Ser. No. 12/929,770, FIG. 18 illustrates a commercially available stereotactic breast core biopsy system adapted for combined simultaneous biopsy and positron emission tomography (PET) combined with computerized tomography (CT) imaging for CNT based parallel X-ray beam brachytherapy treatment planning and with an insert of three sets, thirty parallel microbeams implant that is performed simultaneously with the stereotactic breast biopsy.

Figure 19:
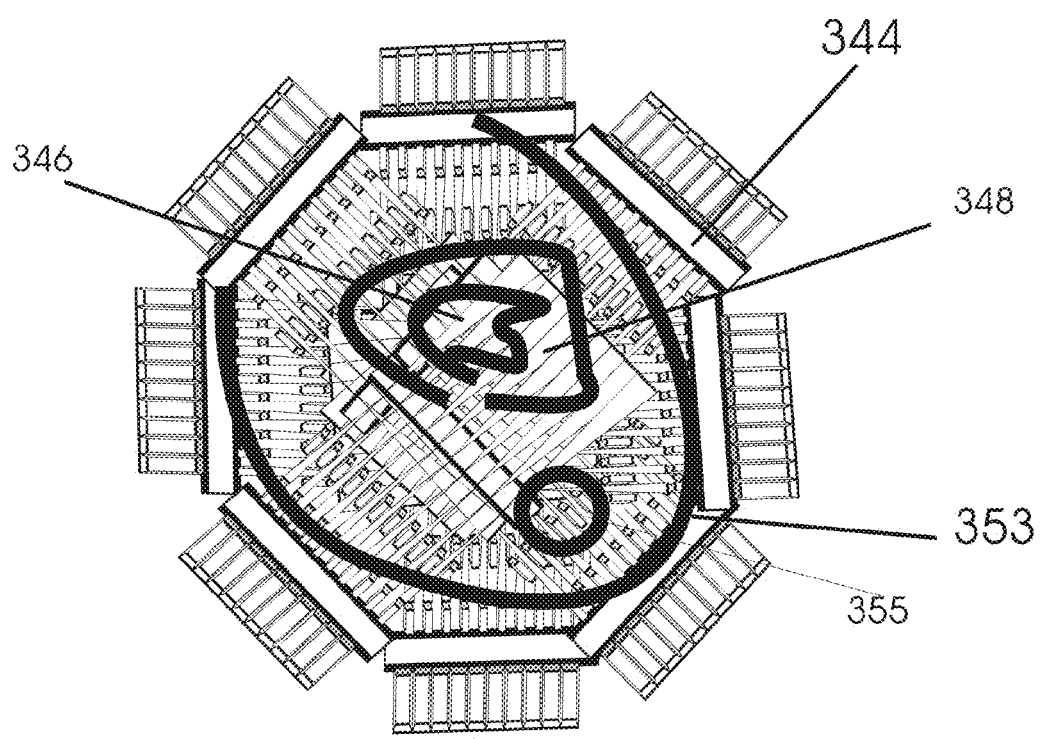

FIG. 19: As in FIG. 19 in the pending patent application Ser. No. 12/929,770, FIG. 19 shows a whole breast interstitial radiation therapy with CNT based X-ray tube's microbeams, eight sets, 10 parallel microbeams each and combined total 80 simultaneous microbeams for an early stage breast cancer and the tumor receiving simultaneous boost radiation from the simultaneous beams passing through the isocenter.

Figure 20:
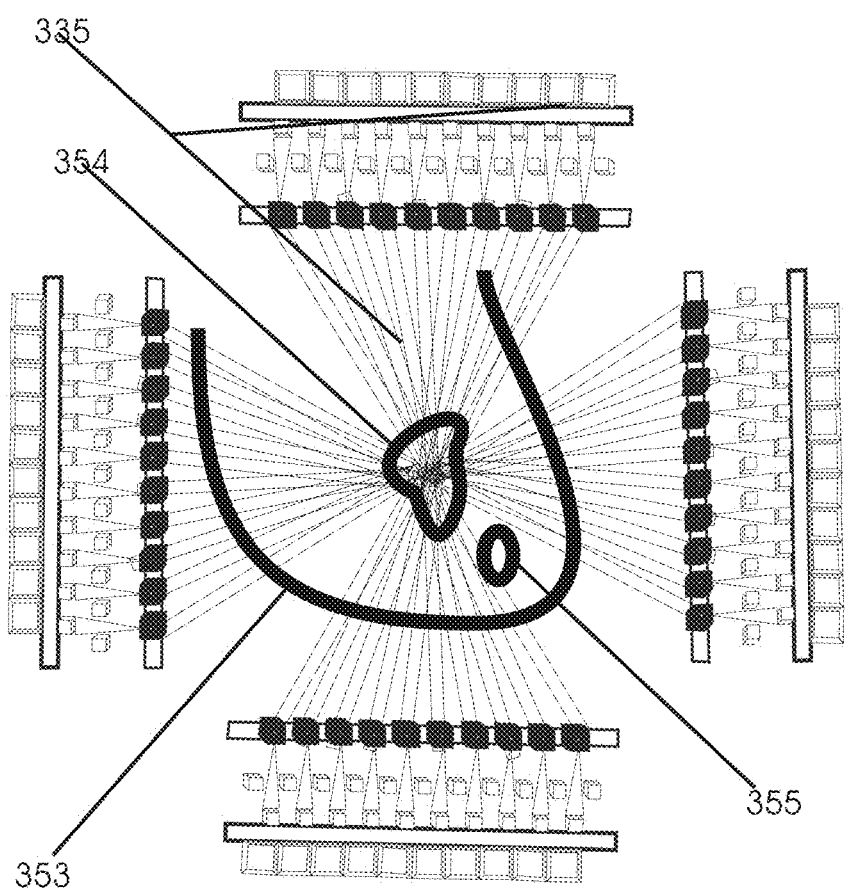
Figure 21:
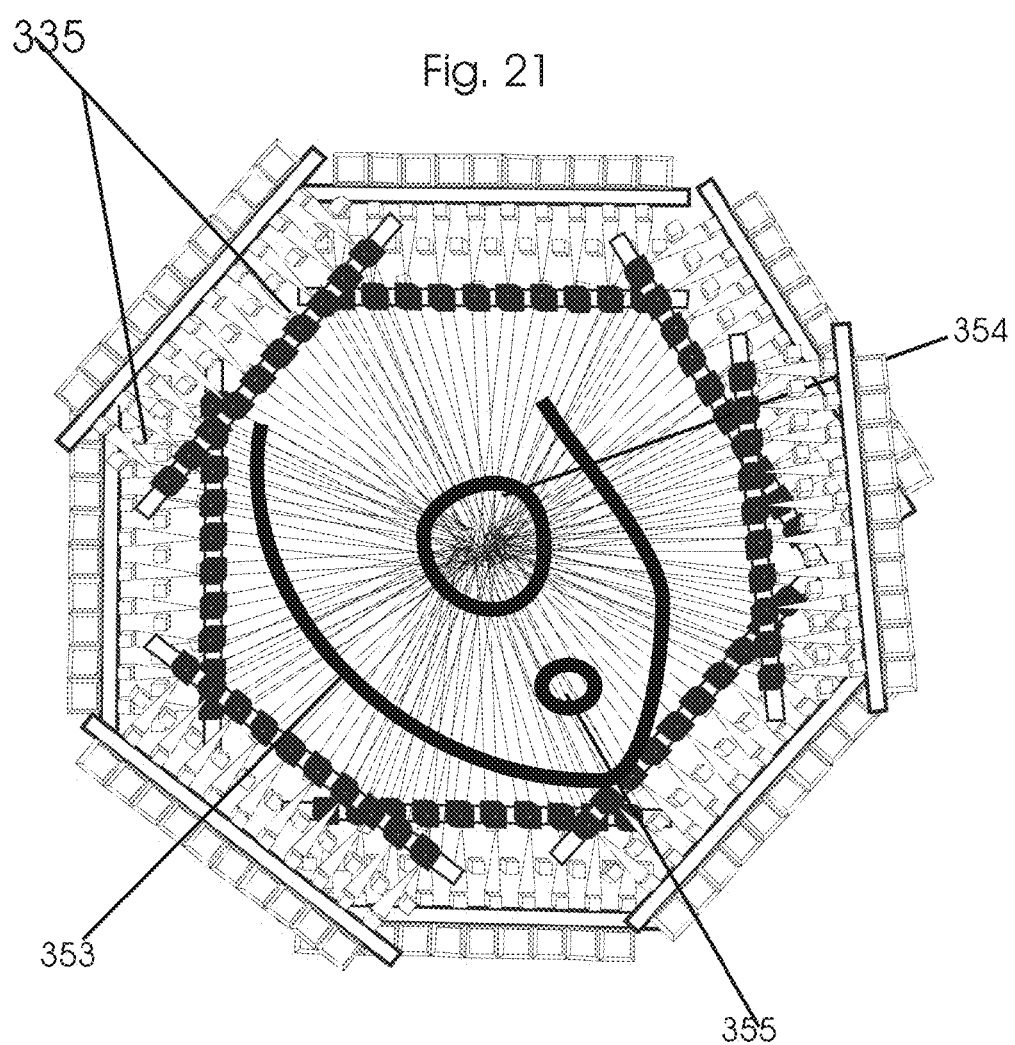
Figure 22:
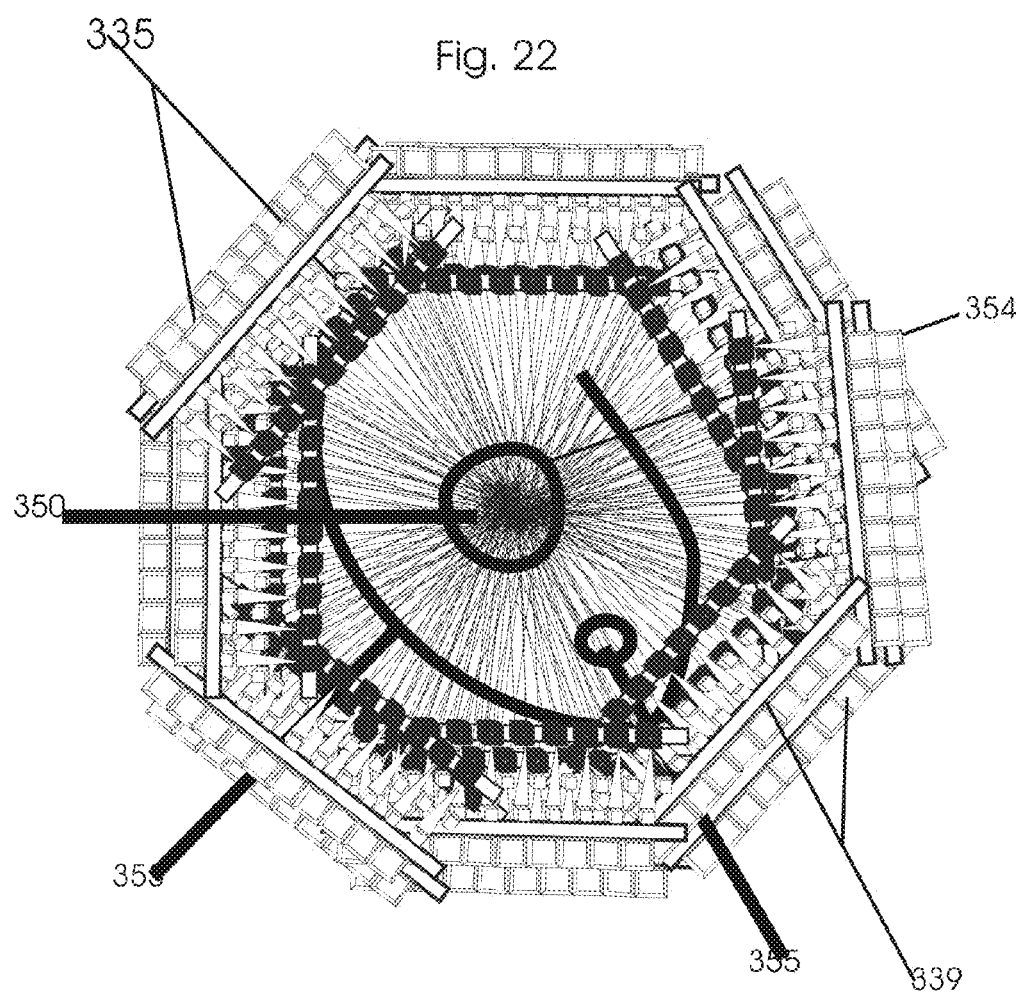

FIG. 20, FIG. 21 and FIG. 22: As in FIG. 21, FIG. 21 and FIG. 22 in the pending patent application Ser. No. 12/929, 770, FIG. 20, FIG. 21 and FIG. 22 illustrates external microbeam radiation therapy to the breast as an example for the whole organ preserving, minimally toxic and curative radiation therapy.

Figure 23:
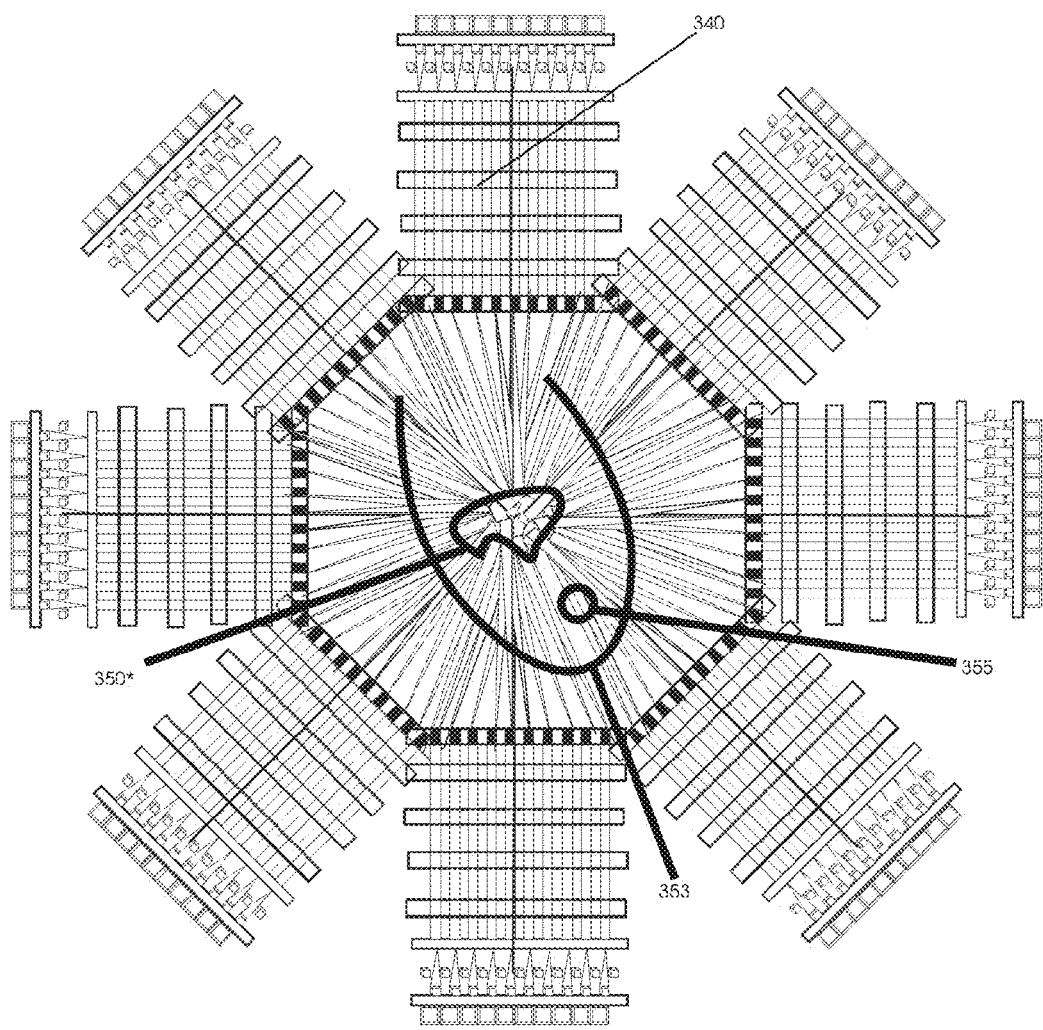

FIG. 23: As in FIG. 23 in the pending patent application Ser. No. 12/929,770, FIG. 23 shows eight sets of CNT based X-ray micro-accelerators, each with 10 minimally diverging microbeams and each accelerator arranged in a circle at 45 degrees apart to radiate a breast cancer.

20. Reference Numerals

254 Micro focus x-ray holding ring with arced collimator
270 Auger transformation characteristic radiations
281 CNT based micro-accelerator
282 MOSEFT
284 MEMS based CNTs holding conductive substrate
285-1 CNT based field emission cathode
286 Carbon nanotubes (CNT)
287 Modified CNTs
287* Focusing electrode
288 CNT based field emission cathode's electron beam
289 Modified CNTs tip loaded with metal oxide crystals
290 Gate electrodes
292 Insulator
293 Beam guide
294 MEMS based power supply
295 nanometer thick collimators
296 Electron guide
298 Transmission anodes
300 X-ray beams
302* water inlet
304 Water outlet
305 Heating and cooling system
306 Water inlets
308 Water outlets
310 System insulator
312 parallel X-ray microbeams
314 Parallel microbeams X-ray tube with 10 beams from 0°
316 Parallel microbeams X-ray tube with 10 beams from 90°
318 Parallel microbeams X-ray tube with 10 beams from 180°
320 Parallel microbeams X-ray tube with 10 beams from 270°
322 Cross firing parallel microbeams from 0 and 180 and 90 and 270 degrees at the center
324 CNT based parallel X-ray microbeam
325 CNT based X-ray tube
326 Accelerating electrodes-1
328 Accelerating electrodes-2
330 Accelerating electrodes-3
332 Accelerating electrodes-4
333 Isocenter
334 Converging multiple beams at the isocenter
335 CNT based X-ray tube with converging focused 10 beams
340 CNT-based 10 microbeams micro-accelerator
341 Selectively switched parallel opposing 6 simultaneous beams
342 10 simultaneous parallel microbeams
343 Beam shaping collimators
344 CNT field emission cathodes based 10-beam interstitial implants
345 Central radiation field generated by 10 cross firing parallel opposed parallel beams
346 High aspects ratio single walled carbon nanotube
347 Enlarged sketch of carbon nanotube
347* Isocentric region spared from radiation
348. CNT doped with nitrogen coated with metal oxide
349 Parallel opposing microbeams
350 Metal oxide
350* Early stage breast cancer with microcalcification
351 Metal oxide crystal
352 Parylene
352* Ductal microcalcification
353 Breast
354 Herringbone arrangement, stacked graphene carbon nanotube
354* Breast cancer 355 Nipple
356 Enlarged sketch of herringbone arrangement, stacked graphene carbon nanotubes
356* CNT based miniature interstitial implant with 10 parallel microbeams
357 Simultaneous 10 parallel microbeam
358 Simultaneous four microbeam electronic brachytherapy system
359A Electronic brachytherapy microbeam peak dose
359B Electronic brachytherapy microbeam valley dose
360 Stereotactic core biopsy systems
361 a patient
362 Stereotactic breast core biopsy system's table
363 Stereotactic system's table
364 PET-CT stereotactic breast core biopsy system
366 Biopsy position
368 CNT based 3 sets, 30 parallel microbeams breast implant
370 Electronic brachytherapy X-ray tube
372 Electrical and cooling water inlets
374 X-ray tube holding ring with cooling running water
376 Water outlet
378 X-ray tube and electrical accessories holding rings
380 Broad beam
382 Tumor
384 CNT based X-ray tube
386 a single micro-X-ray tube assembly for implant
388 micro-X-ray tube filament cathode
390 micro-X-ray tube anode
392 cathode lead cable
394 anode lead cable
396 vacuumed glass tube
398 anode and cathode holding glass container
400 anode and cathode holding glass container
402 water inlet
404 water outlet 27. Description of the Preferred Embodiments FIG. 1 illustrates vertically aligned high aspects ratio single walled carbon nanotube 346 coated with metal oxide 350 in its interior and at metal oxide crystal 351 at its top and coated with parylene 352 at its exterior as cathode for high brightness parallel X-ray microbeam generation with dose rate close to synchrotron for microbeam radiosurgery. An enlarged sketch of carbon nanotube 347 is also shown. Synthesis of CNTs/metal oxide heterostructures are known in the art (2, 48). Such known methods of CNTs/metal oxide heterostructure composite synthesis are adapted to synthesize pyroelectric crystal—CNT combination cathode in this invention. Nitrogen doped CNTs are coated with metal oxide to get a homogenous interior coating of vertically aligned CNT with metal oxide. N-doped CNTs uniformly coated with Pt nanoparticles have superior current density (49).

Vertically aligned high aspect ratio CNT based MEMS are fabricated on silicon and silicon nitrate substrates using known such methods of CNT based MEMS fabrication that is described in the literature before (48). They include the Deep Reactive Ion Etching (DRIE), LIGA Microfabrication and the MEMS fabrication based on the framework of vertically assigned CNT (48). From a framework of patterned film, vertically aligned CNT, are grown and they are filled with the filler material.

The vertically grown high aspects ratio single walled carbon nanotube 346 doped with nitrogen (49) is coated with metal oxide 348 (48). The metal oxides from any of the following groups, like the platinum based nanoparticles, RuOx, $RuO_2$, ZnO, BaO/SrO or other such suitable metal oxides are used for CNT coating. The deposition of the metal oxides on to CNT is done by magnetron sputtering, high thermal evaporation, pulsed laser deposition, chemical vapor deposition or by atomic layer deposition (50). In the microfabrication process, such vertically assigned metal oxide coated CNT is coated with parylene. The parylene coat 352 works both as a pyroelectric coat (51) and as an electric insulator (52). The chemically inert parylene N, Parylene C, Parylene D and parylene HT are excellent electric insulators (52). In the microfabricated MEMS, the parylene film is thus a protective cover for the serially arranged, vertical CNTs with metal oxide. It insulates each of the vertically aligned-metal oxide coated CNTS from electrical short circuits.

In pending patent application Ser. No. 12/929,770, filed Feb. 15, 2011, basic principles of CNT-MEMS based parallel microbeam generating X-ray tubes are described in FIG. 2, FIG. 3 and FIG. 4A. Such CNT-MEMS based parallel microbeam generating x-ray tubes were also shown as incorporated into FIG. 7C, FIG. 7D, FIG. 7E, FIG. 8, FIG. 9, FIG. 10, FIG. 11, FIG. 12, FIG. 13A, FIG. 13B, FIG. 14A, FIG. 14B, FIG. 15C1, FIG. 15C2, FIG. 15D, FIG. 16, FIG. 16, FIG. 17, FIG. 18, FIG. 19, FIG. 20, FIG. 21, FIG. 22 and FIG. 23 in the pending patent application Ser. No. 12/929, 770. In this Continuation-In-Part Application to the previous nonprovisional application, the CNT-MEMS based parallel microbeam generating X-ray tubes described in application Ser. No. 12/929,770 is replaced with modified CNT described in FIG. 1 above or in FIG. 2 or FIG. 3 described below.

FIG. 2 shows herringbone arrangement, stacked graphene carbon nanotubes 354 coated with metal oxide 350 in its interior and pyroelectric crystal parylene 352 in its exterior that generates high brightness parallel X-ray microbeam with dose rate close to synchrotron for microbeam radiosurgery. An enlarged sketch of herringbone arrangement, stacked graphene carbon nanotubes 356 is also shown. As with the natural CNT coating with metal oxides and parylene, herringbone arrangement, stacked graphene carbon nanotubes 354 are coated with any of the following groups of metal oxides 350, the platinum based nanoparticles, RuOx, $RuO_2$, ZnO, BaO/SrO or other such suitable metal oxides. The deposition of the metal oxides on to herringbone arrangement, stacked graphene carbon nanotubes is done by magnetron sputtering, high thermal evaporation, pulsed laser deposition, chemical vapor deposition or by atomic layer deposition (50). In the microfabrication process, such vertically assigned metal oxide coated herringbone arrangement, stacked graphene carbon nanotubes is also coated with parylene. The parylene coat 352 works both as a pyroelectric coat (51) and as an electric insulator (52). The chemically inert parylene N, Parylene C, Parylene D and parylene HT are excellent electric insulators (52). In the microfabricated MEMS, the parylene film is thus a protective cover for the serially arranged, vertical herringbone arrangement, stacked graphene carbon nanotubes with metal oxide. It insulates each of the vertically aligned-metal oxide coated herringbone arrangement, stacked graphene carbon nanotubes from electrical short circuits.

As an alternative embodiment, the natural CNT used to microfabricate MEMS in pending patent application Ser. No. 12/929,770 is replaced with herringbone stacked graphene carbon nanotube coated with metal oxide and parylene in this CIP application. In this case, herringbone stacked graphene carbon nanotube coated with metal oxide and parylene is used to microfabricate the MEMS described in FIG. 2, FIG. 3, FIG. 4A, FIG. 7C, FIG. 7D, FIG. 7E, FIG. 8, FIG. 9, FIG. 10, FIG. 11, FIG. 12, FIG. 13A, FIG. 13B, FIG. 14A, FIG. 14B, FIG. 15C1, FIG. 15C2, FIG. 15D, FIG. 16, FIG. 16, FIG. 17, FIG. 18, FIG. 19, FIG. 20, FIG. 21, FIG. 22 and FIG. 23.

FIG. 3A illustrates array of pyroelectric CNT-metal oxide crystal based parallel microbeam generating MEMS in which either single walled carbon nanotube is coated with metal oxide in its interior and pyroelectric crystal parylene in its exterior or with herringbone arrangement, stacked graphene carbon nanotubes coated with metal oxide in its interior and pyroelectric crystal parylene in its exterior as cathodes to make array of high brightness parallel microbeam with dose rate close to synchrotron for microbeam radiosurgery. They generate very high current densities. The electron emission from the gated cathodes is controlled by very low gate voltages of less than 100 V. The brightness of the beam is 100 to 1,000 times better than the thermionic cathodes. With metal oxide coating in the inferior and parylene film coating in the exterior, the field emission of these CNTs is further increased. It brings the brightness closer to that of synchrotron radiation. They are microfabricated using Spindt microfabrication methods. A wide range of metal oxides including silicon, gallium arsenide, zirconium carbide, hafnium carbide, titanium, niobium, tungsten, lithium are used for the metal oxide coating. They are pyroelectric crystals. Additionally, its exterior coating with parylene makes them more pyroelectric. Parylene is also an electric insulator that protects the parallel arrays of nanotubes from electric current from outside. Modified CNT based MEMS field emission cathode is constructed with the metal-oxide-semiconductor field-effect transistor (MOSEFT) 282 and microelectromechanical systems (MEMS) technology. The CNT based field emission cathode has an array of electron beams producing capability either as individually or as simultaneously when the power is supplied to them from each of the MOFEST 282 and MEMS power supply as individually or as simultaneously. The modified-CNT is deposited on to a MEMS based CNTs holding conductive substrate 284. The power to the CNT-cathode system is controlled by the gate electrodes. The gate electrode is protected with the insulator. The modified CNTs 287 and the modified CNTs tip loaded with metal oxide crystals 289 generate high current when powered. The modified-CNT based field emission cathode's electron beam 288 is focused towards the transmission anode 298. As the electron strikes the transmission anode, forward propagating parallel X-ray microbeam beam 312 is generated that pass through the beam guide 293. Each of the parallel microbeams is collimated by nanometer thick collimators 295.

FIG. 3B shows an array of parallel microbeam generation with heating and cooling of pyroelectric crystal coated single walled carbon nanotube or herringbone arrangement, stacked graphene carbon nanotubes coated with metal oxide in its interior and pyroelectric crystal parylene in its exterior as cathodes to make array of high brightness parallel microbeam with dose rate close to synchrotron for microbeam radiosurgery. It is similar to the array of parallel microbeam generation described in FIG. 3A except for the heating and cooling of the pyroelectric CNTs with heating and cooling running water or electronic heating and cooling as in electronic devices.

The modified-CNTs 287 are deposited on to MEMS based CNTs holding conductive substrate 284. The CNTs loaded with metal oxide and metal oxide crystals are subjected to heating and cooling to produce pyroelectric high current. The heating and cooling water inlet 302 and water outlet 304 thorough the heating and cooling system 305 heats and cools the metal oxides and metal oxide crystals in the CNTs. The modified CNTs 287 and the modified CNTs tip loaded with metal oxide crystals 289 generate high pyroelectric current when heated and cooled. Its electron beam 288 is focused towards the transmission anode 298. As the electron strikes the transmission anode, forward propagating parallel X-ray microbeam beam 312 is generated that pass through the beam guide 293. Each of the parallel microbeams is collimated by nanometer thick collimators 295.

FIG. 4 is a detailed illustration of the basic structures of a MEMS-X-ray tube based on single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior. For description, both are designated as modified-CNT. Either one of them is replaced with the natural CNT based MEMS described in pending patent application Ser. No. 12/929,770. As an example, MEMS—X-ray tube with 10 parallel microbeams is illustrated here. Except for the modified CNTs, single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior and beam configuration, the structures illustrated here have similarities to FIG. 2 and FIG. 3 in the pending patent application Ser. No. 12/929,770. Modified CNT based MEMS field emission cathode 288 is constructed with the metal-oxide-semiconductor field-effect transistor (MOSEFT) 282 and microelectromechanical systems (MEMS) technology. The 10 CNT based field emission cathode 285 has 10 electron beams producing capability either as individually or as simultaneously when the power is supplied to them from each of the 10 MOFEST 282 and MEMS power supply 294 as individually or as simultaneously. The modified-CNT 286 is deposited on to a MEMS based CNTs holding conductive substrate 284. The power to the CNT-cathode system is controlled by the gate electrode 290. The gate electrode 290 is protected with the insulator 292. The modified-CNT based field emission cathode's electron beam 288 is focused towards the transmission anode 298 by the electron guide 296. As the electron strikes the transmission anode, forward propagating parallel X-ray microbeam beam 312 is generated. The cathode-anode system is placed in a vacuum chamber 302. A water cooler with water inlet and outlets 304 is attached to the anode-cathode system. Water flows through the water inlet 306 and water outlet 308. The nanometer and millimeter sized, CNT based MEMS-X-ray tube and interstitial implants are the smallest radiation therapy systems. The whole system is encased into a system insulator 310 (not shown here) for easy handling and its insertion into implant catheters when this or its modified versions are used for interstitial implants.

Figure 5:
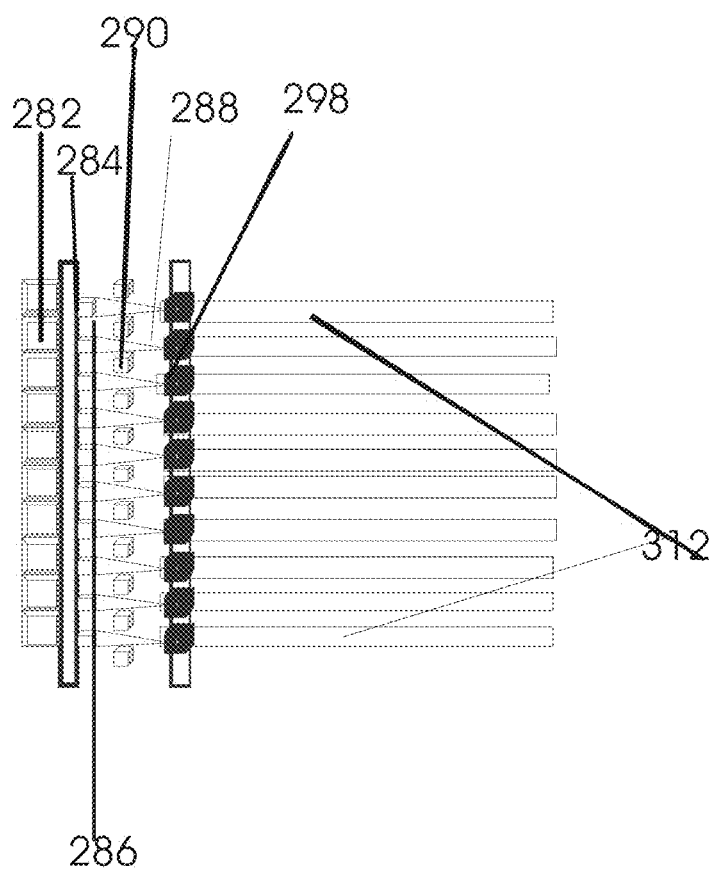
FIG. 5 is another illustration of the basic structures of a modified CNT based single set, 10 simultaneous parallel microbeams X-ray tube.

FIG. 5 is another illustration of the basic structures of a modified CNT based single set, 10 simultaneous parallel microbeams X-ray tube. Except for the modified CNTs, single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior and beam configuration, the structures illustrated here have similarities to FIG. 3 in the pending patent application Ser. No. 12/929,770. Like in FIG. 4 above, the 10 CNT based field emission cathode 285 has 10 electron beams producing capability either as individually or as simultaneously when the power is supplied to them from each of the 10 MOFEST 282 as individually or as simultaneously. There are 10 modified-CNT 286 cathode sources. The CNT is deposited on to a MEMS based CNTs holding conductive substrate 284. The power to the CNT-cathode system is controlled by the gate electrode 290. The CNT based field emission cathode's electron beam 288 is focused towards the transmission anode 298. As the electron strikes the transmission anode, forward propagating parallel X-ray microbeams 312 is generated.

FIG. 6 shows a single set, 10-beam MEMS electron accelerator based on modified carbon nanotube field emission (mCNT-FE Accelerator). As described under FIG. 4, the principles of this MEMS electron accelerator are the same except for the modified CNTs, single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior and beam configuration, the structures illustrated here have similarities to FIG. 4A in the pending patent application Ser. No. 12/929,770. Here, the electron is accelerated by changing the polarity of the electrical current that works as a drift tube. The electron so accelerated strikes the transmission anode generating the forward propagating low energy X-ray beam. Using the MEMS and the MOSEFT technologies, the miniaturized cathode-anode assembly is microfabricated. Details of the X-ray tube microfabrication are described under FIG. 4. Here, a basic X-ray tube is constructed as described in FIG. 4. However only its basic features like the MOFESFT 282, MEMS based CNTs holding conductive substrate 284, CNT based field emission cathode 285, modified carbon nanotubes (CNT) 286, modified CNT based field emission cathode's electron beam 288, the gate electrodes 290, and the transmission anodes 298 are shown. The CNT based field emission cathode's electron beam 288 is focused by the focusing electrode 287 that lets the electron to pass through its pin hole openings (not shown) towards the accelerating electrodes. The accelerating electrodes-1, 326, accelerating electrodes-2, 328, accelerating electrodes-3, 330 and accelerating electrodes-4, 332 acts like a drift tube that accelerates the electron like in a linear accelerator. The electron beam passes through the narrow apertures in the accelerating electrodes (not shown). Each beams passes through its respective aperture in the accelerating electrodes. The focusing electrode 287* and the changing polarity of the accelerating electrodes keeps the electron beam focused and accelerated. It passes through the apertures in the accelerating electrodes. The accelerated electron strikes the transmission anode 298 that generates the forward propagating parallel microbeam. The other features that are shown in FIG. 4 for the CNT based x-ray tube like the vacuum, cooling the insulation etc are not repeatedly illustrated here.

FIG. 7C illustrates intraoperative parallel microbeam radiation to a tumor as described under FIG. 7C in the pending patent application Ser. No. 12/929,770 but with the exception that modified CNTs, single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT in this Continuation-in-Part application. Otherwise, the structures illustrated here have similarities to FIG. 7C in the pending patent application Ser. No. 12/929,770. Four modified CNT based X-ray tube 384 is shown as placed on to the X-ray tube holding ring with cooling running water 374 with water outlets 376 and on to the X-ray tube and electrical accessories holding rings 378. The X-ray tubes are placed at 0, 45, 90 and 135 degrees apart. Their parallel microbeams are shown as radiating a tumor 380. The 25 to 75 μm wide parallel microbeams are spaced at 500 μm apart. It radiates the normal tissue in the peak region at 100% of the dose and spears the valley region from higher dose radiation by having only about 10% or less of the peak radiation. Hence high dose, 100-500 Gy single fraction curative intraoperative radiation therapy with no or minimal toxicity to normal tissue is made possible. The dose deficiency in the valley regions in between the microbeams is filled by the scatter and characteristic radiation and the k, 1, m, n shell Auger radiation that is produced by tuning the energy of the X-ray beam to the binding energy of the high Z-element that is bound or implanted to the tumor.

FIGS. 7D and 7E shows four sets of CNT based micro-accelerators 281 and their simultaneous 10 parallel microbeams 357 radiating a surgically exposed tumor. FIG. 7D and FIG. 7E shows intraoperative parallel microbeam radiation to a tumor as described under FIG. 7D and FIG. 7E in the pending patent application Ser. No. 12/929,770 but with the exception that modified CNTs, single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) in this Continuation-in-Part application. Otherwise, the structures illustrated here have similarities to FIG. 7D and FIG. 7E in the pending patent application Ser. No. 12/929,770. The modified CNT-based micro-accelerators 281 are attached to the X-ray tube and electrical accessories holding ring 378 and X-ray tube holding ring with cooling running water 374 at 0, 45, 135 and 270 degrees. In FIG. 7E, the modified CNT-based micro-accelerators are 281 are attached to the X-ray tube and electrical accessories holding ring 378 and X-ray tube holding ring with cooling running water 374 at 0, 45, 90 and 135 degrees. The heat generated by the miniature micro-accelerators is transferred to the circulating water that runs through the water outlets 376. Simultaneous 10 parallel microbeams 357 from each of the four CNT based micro-accelerators expose the tumor 382 as they intersect at the site of the tumor 382. The parallel microbeams do not cross each other after their intersection through the tumor 382. Hence the peak and valley dose in between the parallel microbeams do not intermix in the normal tissue. It assures minimal radiation to the normal tissue and rapid normal tissue recovery from radiation. Thus, the single fraction radiation to the tumor is in the range of about 100-1,000 Gy and higher. Because of the high dose rate of up to about 20,000 Gy/sec, the beam exposure lasts only a fraction of a second.

FIG. 8 illustrates four sets of CNT based X-ray tubes 312 with parallel microbeams arranged within a circle and each X-ray tube having 10 parallel microbeams, parallel microbeams X-ray tube with 10 beams from 0° 314, parallel microbeams X-ray tube with 10 beams from 90° 316, parallel microbeams X-ray tube with 10 beams from 180° 318. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) in this Continuation-in-Part application. Otherwise, the structures illustrated here have similarities to the former FIG. 8 in the pending patent application Ser. No. 12/929,770. In FIG. 8, four sets of modified CNT based X-ray tubes 312 with parallel microbeams arranged within a circle and each X-ray tube having 10 parallel microbeams, parallel microbeams X-ray tube with 10 beams from 0° 314, parallel microbeams X-ray tube with 10 beams from 90° 316, parallel microbeams X-ray tube with 10 beams from 180° 318, and parallel microbeams X-ray tube with 10 beams from 270° 320. The cross firing parallel microbeams from 0 and 180 and 90 and 270 degrees at the center 322 is shown as exposing a square field at the center with 40 simultaneous parallel microbeams.

FIG. 9: As in FIG. 9 in the pending patent application Ser. No. 12/929,770, FIG. 9 in this Continuation-In-Part-Application shows a miniaturized interstitial implant with modified CNTs based X-ray tube and its basic structures. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) in this Continuation-in-Part application. The modified CNT based parallel X-ray microbeam 324 is switched as simultaneous microbeams, single microbeams or sequential microbeams. The 10 CNT based field emission cathode 285 has 10 electron beams producing capability either as individually or as simultaneously when the power is supplied to them from each of the 10 MOFEST 282. There are 10 modified carbon nanotube 286 cathode sources. The CNT is deposited on to a MEMS based CNTs holding conductive substrate 284. The power to the CNT-cathode system is controlled by the gate electrode 290. The CNT based field emission cathode's electron beam 288 is focused towards the transmission anode 298. As the electron strikes the transmission anode, forward propagating parallel X-ray microbeams 324 is generated. Such a CNT based X-ray tube 325 is shown in the insert.

FIG. 10: As in FIG. 10 in the pending patent application Ser. No. 12/929,770, the FIG. 10 in this Continuation-In-Part-Application shows seven CNT based external electron accelerates with combined 70 microbeams that are passing through the isocenter and they intersect at the isocenter. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) in this Continuation-in-Part application. This set of miniaturized, CNT based accelerators includes 10-beam miniature accelerator-1, 326, 10-beam miniature accelerator-2, 328, 10-beam miniature accelerator-3, 330, 10-beam miniature accelerator-4, 332, 10-beam miniature accelerator-5, 334, 10-beam miniature accelerator-6, 336, and 10-beam miniature accelerator-7, 338. Their combined microbeams meet at the isocenter 333. These accelerators are used for low energy contact treatment as in low energy Grenz ray therapy to an operatively exposed tumor from multiple angles and with multiple simultaneous beams. Alternatively, their higher energy version is used as multiple external microbeam sources for intraoperative radiation. Their interstitial version is used for simultaneous up to 70 microbeam interstitial brachytherapy with CNT based miniature X-ray tubes. Its other use includes treating skin tumors either as contact-Grenz ray therapy or as interstitial brachytherapy.

FIG. 11: As in FIG. 11 in the pending patent application Ser. No. 12/929,770, the FIG. 11 in this Continuation-In-Part-Application illustrates eight units of modified CNT based field emission accelerators, each with 10 parallel microbeams. They converge at the isocenter. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) in this Continuation-in-Part application.

The simultaneous beams additive dose is at the isocenter 333 where the treating tumor is located. Each micro beams passes through the normal tissue towards the isocenter 333. Such microbeam facilitates the broad beam effect at the isocenter but with near parallel beam effects within the normal tissue through which they pass towards the isocentric tumor. The single fraction dose that is administered at the isocenter is in the range of 100 to 1,000 Gy. Because of the parallel microbeam radiation the normal tissue toxicity is avoided or minimized.

FIG. 12, FIG. 13A and FIG. 13B: As in FIG. 12, FIG. 13A and FIG. 13B in the pending patent application Ser. No. 12/929,770, the FIG. 12, FIG. 13A and FIG. 13B in these Continuation-In-Part-Application shows miniaturized 10 parallel beams accelerator for interstitial implant. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) in this Continuation-in-Part application.

The external beam radiation and interstitial implant radiation with modified CNT based 10-beam micro-accelerators 340 and their 10 simultaneous parallel microbeams 342 are shown. FIG. 13A illustrates two orthogonally placed modified CNT based 10 microbeams micro-accelerators 340, one at 0 degree and the other at 90 degrees with their parallel microbeams cross-firing at the isocenter where the planning tumor volume 348 is located. The parallel microbeams spaced at 500 µm apart radiates the normal tissue in the peak region at 100% of the dose and spears the valley region from higher dose radiation by having only about 10% or less of the peak radiation. Hence the parallel microbeams with 500 µm spacing in between is used to treat a tumor with curative dose of 100 to 1,000 GY or 500-5,000 Gy without causing much toxicity to the normal tissue. The volume treated is increased with an array of such MEMS accelerators described in this application elsewhere.

FIG. 13B shows four such miniaturized modified CNT based accelerator's 340 combined 40 parallel opposing microbeams 349 exposing a panning tumor volume 348 bearing region that forms a square radiation field. The parallel opposing microbeams spaced at 500 µm apart radiates the normal tissue in the peak region but still spears the valley region from higher dose radiation. Hence with such parallel opposed microbeams with 500 µm spacing in between treats a tumor with 100-1,000 Gy and higher curative dose. The volume treated is increased with an array of such MEMS accelerators described in this application elsewhere.

FIG. 14A: As in FIG. 14 in the pending patent application Ser. No. 12/929,770, the FIG. 14 in this Continuation-In-Part-Application shows selectively switched parallel opposing 6 simultaneous beams 341 from four sets of miniaturized CNT based 10 microbeams micro-accelerators 340 that covers the planning tumor volume 348 but with sparing of the isocentric region where no tumor is located. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) in this Continuation-in-Part application. By selectively switching of the microbeams, the spared isocentric region from radiation 347* is created. It functions as a superior collimation of the beams. Six beams from each of the accelerator set's 10 beams are selectively switched on. The beam width is selected as 25-75 μm width. They are spaced at 200-400 μm apart. Its additive broad beam effect at the isocentric tumor site and parallel beam effect in the normal tissue spares the normal tissue while the tumor tissue is treated with high single fraction dose of 100-1,000 Gy that sterilize both the differentiated tumor cells and the cancer stem cells. It avoids developing adaptive resistance to radiation.

FIG. 14B illustrates the parallel microbeams 342 from a set of miniature accelerators placed at 0 and 90 degrees. As these parallel microbeams intersecting at the isocenter 333, they do not overlap the normal tissue outside the isocenter 333. The valley dose outside the isocenter is very low. This spares the normal tissue and hence dose in the range of 100-1,000 Gy and higher can be administered to an isocentric tumor.

FIG. 15A shows a breast 353 with an early stage breast cancer 350 and ductal microcalcification 352. The early stage breast cancer 350 and the ductal microcalcifications are shown close to the nipple 355.

FIG. 15B, illustrates an early stage breast cancer 354 with ductal microcalcification 352 as treated with a single set electronic brachytherapy X-ray tube 370. Under sterile conditions, the microbeam generating micro electronic brachytherapy X-ray tube 370 is inserted into the breast and threaded into the ductal microcalcification 352 containing early stage breast cancer 354. The tumor is radiated with microbeam spaced at 25 to 75 micrometer apart to high doses as described in this invention.

FIG. 15C-1 shows a single micro-X-ray tube assembly for implant 386. The micro-X-ray tube filament cathode 388 and the micro-X-ray tube anode 390 are enclosed within a vacuumed glass tube 396. The cathode lead cable 392 and anode lead cable 394 supplies the electrical power to the cathode and the anode. The X-ray produced from the anode passes through the window 398 in the forward direction of the arrow as is shown in the illustration. The vacuumed glass tube 396 containing the cathode and the anode is enclosed in the vacuumed tube and anode and cathode holding glass container 400. The anode and the cathode are cooled with circulating water that flows through water inlet 402 and water outlet 404. Four such micro-X-ray tubes are put together that makes a single micro-X-ray tube assemblies for the implant 358. Other examples of miniature X-ray sources like those with cold emission cathode is also adapted for interstitial micro-X-ray tube implant. A few mm sized micro-X-ray tubes are used for vascular radiation. Multiple cold emission cathode micro-X-ray tubes of a few mm in size are also assembled together (not shown here) for multiple simultaneous microbeam implant radiation therapy that is described in this invention The FIG. 15C-2 illustrates an early stage breast cancer 354 as treated with a single simultaneous four microbeam beam electronic brachytherapy system 358. The microbeams are spaced at 500 μm from each other. The electronic brachytherapy microbeam peak dose 359A and the electronic brachytherapy microbeam valley dose 359B are shown in the insert. While the electronic brachytherapy microbeam peak dose 359A has 100% of the microbeam dose, the electronic brachytherapy microbeam valley dose 359B is only about 10% of the peak dose. Because of this low valley dose, normal tissue tolerance to radiation is increased significantly, in the range of 500 to 5,000 Gy when the width of the microbeam in the range of 25-75 μm.

FIG. 15D illustrates an early stage breast cancer 354 treatment with four separate simultaneous four microbeam electronic brachytherapy systems 358. The first of the four microbeam electronic brachytherapy systems 358-1 microbeam set is inserted at 0-degree, second 358-2 is inserted at 45-degree, the third 358-3 is inserted at 135-degree and the fourth 358-4 is inserted at 220 degrees. Their combined 16 microbeams are shown as intersecting at the isocentric tumor 354. The electronic brachytherapy microbeam peak dose 359A and the electronic brachytherapy microbeam valley dose 359B are shown in the insert. As described under FIG. 15C, while the electronic brachytherapy microbeam peak dose 359A has 100% of the microbeam dose, the electronic brachytherapy microbeam valley dose 359B has only about 10% of the peak dose. Because of this low valley dose, normal tissue tolerance to radiation is increased significantly, in the range of 500 to 5,000 Gy when the width of the microbeam in the range of 25-75 μm (54, 55). The valley dose in between the 500 μm spaced microbeams where they intersect is enhanced by the scattered and the k, l, m, n shell characteristic and Auger radiation. It is also enhanced by selectively tuning the energy of the microbeam to the binding energies of the k, l, m, n shell of the high Z elements that is locally bound or implanted. The scattered and characteristic X-rays have predominantly low energy radiation, in the range of 10-20 keV. It's RBE is close to that of high LET radiation. This RBE is further enhanced by the sixteen simultaneous beam's additive high dose and dose rate. Single fraction higher dose and dose rate interstitial brachytherapy with 16 simultaneous microbeam with 4 simultaneous four microbeam electronic brachytherapy systems 358 improves the whole breast preservation radiation therapy at doses 100-1,000 Gy and higher without normal tissue toxicity and whole breast preservation without breast deformity and cancer stem cell sterilization that assures no or rare local tumor recurrence. However, due to lower dose rate of individual beams, its relative treatment time is longer than when a tumor is treated with CNT based X-ray tubes with dose rate close to 20,000 Gy/sec.

FIG. 16 shows an early stage breast cancer as treated with a CNT based miniature interstitial implant with 10 parallel microbeams. The breast 353 is shown with the implanted 10 parallel microbeam 356. This miniature accelerator structures are described in FIG. 3. The simultaneous 10 parallel microbeam 357 is shown as radiating the entire region of micro calcification. The insert shows the interstitial implant 356*. Its basic structures are described in detail under FIG. 3. Because of the parallel microbeam that radiates the tumor tissue with high intensity radiation while sparing the adjacent normal tissue much higher single fraction radiation to the tumor bearing region is administered. Such high dose radiation is not feasible with conventional alternative external or electronic brachytherapy or brachytherapy with radioactive isotopes.

In FIG. 17, the same early stage breast cancer 354 with ductal microcalcification 352* that is shown is illustrated with 3 sets of miniature interstitial implant with 10 parallel microbeams 356*, with a total of 30 parallel microbeams 357. This 30 beam parallel microbeams generates a broad beam effect at the tumor site of the implant while in the rest of the tissue thorough which it travels, it is parallel to each other.

FIG. 18: As in FIG. 18 in the pending patent application Ser. No. 12/929,770, FIG. 18 illustrates a commercially available stereotactic breast core biopsy system adapted for combined simultaneous biopsy and positron emission tomography (PET) combined with computerized tomography (CT) imaging for CNT based parallel X-ray beam brachytherapy treatment planning and with an insert of three sets, thirty parallel microbeams implant that is performed simultaneously with the stereotactic breast biopsy. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) based interstitial implant in this Continuation-in-Part application.

After the mammography, any patients with suspected microcalcification will generally undergo diagnostic biopsy. For those patients wishing to have whole breast preservation with minimal or no cosmetic deformity will be advised to have combined minimally invasive stereotactic breast core biopsy or needle biopsy and if the immediate online, onsite histological analysis of the biopsy specimen shows definitive evidence of carcinoma, then to have immediate, same settings single session interstitial X-ray based brachytherapy to the tumor site alone or combined with whole breast radiation therapy with parallel or converging microbeams. The converging microbeam is almost parallel during its course of travel to the region where the tumor is located. The multiple parallel microbeams from different angles form a broad beam as they cross the tumor.

The treatment with parallel microbeam facilitates treating the tumor at much higher dose, 100-1,000 Gy and higher that kills the "differentiated tumor cells and the dormant cancer stem cell. In this instance, the question of residual tumor at the tumor bed and or at the resection margin and the presence of radiation resistant cancer stem cells becomes a mute question. The total dose administered by the methods of present conventional fractionated radiation therapy is in the range of 50 to 60 Gy within a prolonged treatment time. Hence it does not sterilize all the "differentiated" tumor cells. More importantly, the Cancer stem cells are not much affected by this inefficient, low dose radiation. Hence the importance of tumor free tumor bed and resection margin when a patient is treated by the conventional broad beam fractionated low total dose radiation becomes a mute question. Treating a tumor with multiple simultaneous parallel microbeams and at much higher dose of 100 to 1,000 Gy in a single fraction with less toxicity to normal tissue due to rapid healing by the normal tissue proliferation to the former tumor tissue site and leaving no residual cancer stem cells makes such treatment more curative. Treating the tumor at the time of its first surgical intervention in the form of stereotactic needle biopsy eliminates the tumor recurrence from the implanted tumor cells in the needle track. By avoiding the biopsy after the first needle biopsy, re-biopsy if the resection margin is positive, avoiding the lumpectomy or segmental mastectomy with the intent to preserve the breast and the present methods of postoperative radiation therapy all leaves cosmetically much deformed breast. The single fraction radiation therapy instead of 5 to 6 weeks duration radiation therapy is also convenient and economically most beneficial to the patient, to the socially concerned community and for healthcare planners and providers all alike. These are some of the advantages of the concomitant simple stereotactic needle biopsy combined with onsite immediate curative radiation therapy. A patient 361 is shown as lying with her arm stretched and her breast fixed in stereotactic core needle biopsy position 366 below the cut portion of the extended head side of the stereotactic breast core biopsy system's table 362. The stereotactic breast core biopsy system 360 is incorporated with a PET-CT-stereotactic core biopsy system 364. Stereotactic breast core biopsy is taken from the breast fixed in stereotactic breast core needle biopsy position 366. The biopsy specimen is processed immediately. While the specimen is being processed for histology, the stereotactic system's table 363 with the patient 361 is advanced to the PET-CT-stereotactic core biopsy system 364. The treatment planning PET-CT with patient in stereotactic treatment position is taken and a preliminary online treatment planning is done. For those patients strongly suspected to have breast cancer, pre-biopsy $^{18}$F-glucose is administered as the tracer for the PET scan. This PET scan also serves for the future follow up of the patient's disease. If the biopsy specimen confirms the presence of cancer, immediate final treatment planning is completed and the multiple or single set, 10 beams each, parallel microbeam breast implant is performed. In this case, a CNT based 3 sets, 30 parallel microbeams breast implant 368 is shown in the insert which is described in detail in FIG. 17.

FIG. 19: As in FIG. 19 in the pending patent application Ser. No. 12/929,770, FIG. 19 shows a whole breast interstitial radiation therapy with CNT based X-ray tube's microbeams, eight sets, 10 parallel microbeams each and combined total 80 simultaneous microbeams for an early stage breast cancer and the tumor receiving simultaneous boost radiation from the simultaneous beams passing through the isocenter. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) based interstitial implant in this Continuation-in-Part application. Eight sets of CNT field emission cathodes based 10 beam interstitial implants 344 are shown as partially implanted into the breast 353 from every 45 degree angles. The breast 353 with the gross tumor volumes (GTV), 346 and the planning tumor volume (PTV) 348 are well covered by these 80 simultaneous microbeams. It facilitates concomitant single session whole breast radiation and radiation therapy to the tumor with higher dose.

FIG. 20, FIG. 21 and FIG. 22: As in FIG. 21, FIG. 21 and FIG. 22 in the pending patent application Ser. No. 12/929, 770, 20, FIG. 21 and FIG. 22 illustrates external microbeam radiation therapy to the breast as an example for the whole organ preserving, minimally toxic and curative radiation therapy. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) based interstitial implant in this Continuation-in-Part application. FIG. 20 illustrates a forty focused simultaneous external beam radiation to an early stage breast cancer with four sets of CNT based X-ray tube with converging focused 10 beams 335 and each set's 10 beams as focused to the isocentric tumor 354. Four sets of external CNT based X-ray tubes with converging focused 10 beams 335 are shown as converging into the isocentric tumor 354 in the breast 353 with nipple 355. The forty simultaneous microbeams, all converging at the isocentric tumor renders high additive dose and dose rates but not at high dose as it is possible with treating a tumor with parallel micro beams. It is because the loss of valley dose effect in sparing of the normal tissue. Still, the additive dose of all the beams is so high that it sterilizes the "differentiated" and the dormant tumor stem cells that could otherwise cause later tumor recurrence. It is a simple, single session external curative radiation to the tumor. It could also be used as concomitant boost or as boost radiation after completing the initial whole breast radiation. FIG. 21 illustrates the method of whole breast radiation with concomitant high dose to the tumor with eighty focused simultaneous external microbeam from CNT based X-ray tubs and each set's 10 beams as focused to the isocenter and with higher dose to the isocentric tumor from all the eighty beams converging at the isocenter. This method of microbeam radiation is better tolerated due to the capacity for the normal tissue regeneration and sterilization of the tumor tissue at the isocenter. Eight sets of external CNT based X-ray tubes, each having converging focused 10 beams 335 are shown as converging into the isocentric tumor 354 in the breast 353 with nipple 355 and also diffusely radiating the whole breast. The eighty simultaneous microbeams, all converging at the isocentric tumor renders high additive dose and dose rates that sterilizes the "differentiated" and the dormant tumor stem cells that could otherwise cause later tumor recurrence. It is a simple, single session external CNT based X-ray whole breast radiation and curative dose radiation to the isocentric tumor. FIG. 22 is similar to that illustrated in FIG. 21 but with 160 external CNT based X-ray microbeams.

FIG. 23: As in FIG. 23 in the pending patent application Ser. No. 12/929,770, FIG. 23 shows eight sets of CNT based X-ray micro-accelerators, each with 10 minimally diverging microbeams and each accelerator arranged in a circle at 45 degrees apart to radiate a breast cancer. Single walled carbon nanotube coated with metal oxide in its interior and pyroelectric crystal parylene in its exterior or herringbone arrangement, stacked graphene carbon nanotubes coated with metal oxide in its interior and pyroelectric crystal parylene in its exterior is used as modified CNT (modified CNT) based interstitial implant in this Continuation-in-Part application. Eight micro CNT-based X-ray micro accelerators are described under FIG. 11. In this FIG. 23, their microbeams are directed towards the isocenter where a breast tumor is located. It is shown here as an example of whole organ preserving radiation therapy with multiple simultaneous microbeams, in this instance with combined 80 microbeams. The eight CNT based 10 beams microaccelerator's 340 eighty microbeams encircles the whole breast 353 and is focused at the isocenter where the early stage breast cancer with microcalcification 350* is located. Because of the microbeams, single fraction high additive dose to the tumor that is at the isocenter is delivered, it sterilizes both the "differentiated" and the "tumor stem cell" and avoids adaptive resistance to radiation therapy. It prevents the future tumor recurrence. These simultaneous microbeams's additive dose rate can reach close to that of high flux synchrotron radiation. It is very effective for tumor sterilization even for those tumors known to be very much resistant to radiation like the glioblastoma multiforme. These beams could be switched on or off individually. It facilitates treating the tumor with desired intensity modulation that conforms to the 3-D shape and configuration of the tumor.

21. Methods of Operation

MEMS based on modified carbon nanotube are used for high dose rate 100-1,000 Gy and higher single faction radiosurgery. Carbon nanotube is coated with metal oxide in its interior and pyroelectric crystal parylene in its exterior. Carbon nanotube or carbon nanotube variant herringbone arrangement, stacked graphene coated with metal oxide in its interior and pyroelectric crystal parylene in its exterior is made as modified CNT (modified CNT). MEMS X-ray tubes based on modified CNTs are used for intraoperative contact or interstitial implant radiosurgery in this Continuation-in-Part-Patent-Application to pending patent application Ser. No. 12/929,770. The Methods of Operation described in pending patent application Ser. No. 12/929,770 using unmodified carbon nanotube are also applicable in this Continuation-in-Part-Patent-Application. MEMS—micro X-ray tubes or micro accelerators are brought close to surgically exposed tumors under sterile conditions. The source distance to the tumor is determined optic distance indicator devices for dose calculations. It is well known in the art of radiation therapy. This distance is also determined by manual measurements with the aid of inspection and palpation of the surgically exposed tumor in relation to the X-ray sources. For interstitial implants, the methods of brachytherapy are employed. The encapsulated MEMS based microaccelerators are inserted into the tumor tissue as illustrated in FIG. 9, FIG. 13A, FIG. 13B, FIG. 15C-1, FIG. 15C-2, FIG. 15D, FIG. 16, FIG. 17, FIG. 18, and FIG. 19. Larger field interstitial parallel microbeam radiosurgery is applied with arrays of such modified carbon nanotube based MEMS. Broad areas of contact brachytherapy-radiosurgery are performed with arrays of MEMS X-ray tubes or micro accelerators that form nearly fixable sheets when loaded on to flexible substrates. Such filed emission field display like format MEMS X-ray tubes are shown in FIG. 3A and FIG. 3B. Contact parallel microbeam X-ray brachytherapy-radiosurgery is performed with systems illustrated in FIG. 7C, FIG. 7D, FIG. 7E, FIG. 8, FIG. 10, FIG. 11, FIG. 14A, and FIG. 14B. MEMS with carbon nanotube coated with metal oxides and loaded with metal oxide crystals and parylene coating generates high brightness X-ray beams with dose rate in the range of 10-20,000 per seconds that is close to synchrotron radiation's dose rate. MEMS X-ray systems generates parallel microbeam when electrical power is applied to it; otherwise it has no radiation. Heating and cooling by running water or by electronic cooling and heating are also used for pyroelectric high current generation in modified carbon nanotubes coated and loaded metal oxides and metal oxide crystals that generates pyroelectric current when intermittently heated and cooled. The electron beam generated by the MEMS based cathodes with modified CNTs is modulated towards nanometer thick anode that generates high brightness microbeam. Array of such MEMS based X-ray tubes and microaccelerators generate parallel microbeams. They are collimated by built in nanometer thick collimators that keep the microbeams as parallel with minimal divergence for parallel microbeam radiosurgery. Further details of such radiation using MEMS based micro X-ray tubes and accelerators are described in the section titled detailed description of the drawings.

What is claimed is:

1. An apparatus for 100 to 1,000 Gy single fraction parallel microbeam radiation therapy comprising:
    a. parallel miniature X-ray sources based on modified carbon nanotube field emission;
    b. carbon nanotubes coated with metal oxide and metal oxide crystal that generates high brightness cathode with dose rate close to synchrotron radiation;
    c. carbon nanotubes insulated with parylene crystals that generates simultaneous high field current and high brightness cathode;
    d. nanometers thick transmission anode that generates high brightness X-ray beam;
    e. micrometers thick collimators that collimates the parallel microbeams;

f. a plurality of modified carbon nanotubes coated with a metal oxide and a metal oxide crystal and insulated with parylene crystals for generating high brightness cathode and parallel X-ray sources emitting parallel microbeams radiations;

g. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated;

h. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for 100 to 1000 Gy parallel microbeam radiosurgery of a tumor;

i. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for 100 to 1,000 Gy single fraction interstitial implant radiosurgery;

j. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for 100 to 1,000 Gy single fraction parallel microbeams radiosurgery with low dose valley regions and high dose regions of the parallel microbeams to spare stem cells from radiation toxicity;

k. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for 100 to 1,000 Gy single fraction parallel microbeams radiosurgery of a tumor to avoid radioresistance caused by daily lower dose radiation therapy and lasting several weeks;

l. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for 100 to 1,000 Gy single fraction parallel microbeams radiosurgery of a tumor to avoid adaptive radioresistance caused by epidermal growth factor in tumors;

m. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for 100 to 1,000 Gy single fraction parallel microbeams radiosurgery of a tumor to avoid adaptive radioresistance caused by high content epidermal growth factor in brain tumors;

n. a plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for 100 to 1,000 Gy single fraction parallel microbeams radiosurgery of a tumor to expose tumor antigens that initiate local and systemic tumor immunity.

2. Apparatus of claim 1 based on carbon nanotubes coated with a metal oxide and a metal oxide crystal and insulated with parylene crystals for generating high brightness cathode and parallel X-ray sources emitting parallel microbeams for 100 to 1,000 Gy single fraction microbeam radiosurgery.

3. Apparatus of claim 1 based on carbon nanotubes coated with a metal oxide and a metal oxide crystal and insulated with parylene crystals for generating high brightness cathode and parallel X-ray sources emitting arrays of parallel microbeams wherein intensity of each of the X-ray sources is modulated for intensity modulated single fraction 100 to 1000 Gy radiosurgery of a surgically exposed tumor.

4. Apparatus of claim 1 based on carbon nanotubes coated with a metal oxide and a metal oxide crystal and insulated with parylene crystals for generating high brightness cathode and parallel X-ray sources emitting parallel microbeams for 100 to 1,000 Gy single fraction contact radiosurgery.

5. Apparatus of claim 1 based on carbon nanotubes coated with a metal oxide and a metal oxide crystal and insulated with parylene crystals for generating high brightness cathode and parallel X-ray sources emitting parallel microbeams for 100 to 1,000 Gy single fraction interstitial implant radiosurgery.

6. A plurality of modified carbon nanotubes coated with a metal oxide and a metal oxide crystal as in claim 1 and insulated with parylene crystals for generating high brightness cathode and parallel X-ray sources emitting parallel microbeams radiations wherein intensity of each of the X-ray sources is modulated for 100 to 1,000 Gy parallel microbeams radiosurgery without much normal tissue toxicity by stem cell migration from low dose valley regions to high dose regions of the parallel microbeams.

7. A plurality of modified carbon nanotubes coated with a metal oxide and a metal oxide crystal and insulated with parylene crystals for generating high brightness cathode and parallel X-ray sources emitting parallel microbeams radiations wherein intensity of each of the X-ray sources is modulated for cancer and cancer stem cell sterilizations single fraction 100 to 1,000 Gy and higher dose parallel microbeams radiosurgery.

8. A plurality of modified carbon nanotubes coated with a metal oxide and a metal oxide crystal as in claim 1 and insulated with parylene crystals for generating high brightness cathode and parallel X-ray sources emitting parallel microbeams radiations wherein intensity of each of the X-ray sources is modulated for single fraction 100 to 1,000 Gy parallel microbeam radiosurgery to avoid radioresistance caused by daily lower dose radiation therapy and lasting several weeks.

9. A plurality of modified carbon nanotubes coated with a metal oxide and a metal oxide crystal as in claim 1 and insulated with parylene crystals for generating high brightness cathode and parallel X-ray sources emitting parallel microbeams radiations wherein intensity of each of the X-ray sources is modulated for 100 to 1,000 Gy single fraction parallel microbeams radiosurgery of a tumor to avoid adaptive radioresistance caused by epidermal growth factor in tumors.

10. A plurality of modified carbon nanotubes coated with a metal oxide and a metal oxide crystal as in claim 1 and insulated with parylene crystals for generating high brightness cathode and parallel X-ray sources emitting parallel microbeams radiations wherein intensity of each of the X-ray sources is modulated for 100 to 1,000 Gy single fraction parallel microbeams radiosurgery of a tumor to avoid adaptive radioresistance caused by high content epidermal growth factor in brain tumors.

11. A plurality of modified carbon nanotubes coated with a metal oxide and a metal oxide crystal as in claim 1 and insulated with parylene crystals for generating high brightness cathode and parallel X-ray sources emitting parallel microbeams radiations wherein intensity of each of the X-ray sources is modulated for single fraction 100 to 1,000 Gy parallel microbeam radiosurgery to expose tumor antigens that initiate local and systemic tumor immunity.

* * * * *